US012642644B2

(12) United States Patent
Slagmolen et al.

(10) Patent No.: US 12,642,644 B2
(45) Date of Patent: Jun. 2, 2026

(54) SCAFFOLD BASED IMPLANTS

(71) Applicant: Materialise NV, Leuven (BE)

(72) Inventors: Pieter Slagmolen, Technologielaan (BE); Inge Famaey, Leuven (BE); Durva Gajjar, Leuven (BE); Giulia Rosellini, Leuven (BE); Dries Vandecruys, Leuven (BE)

(73) Assignee: Materialise N.V., Leuven (BE)

( * ) Notice: Subject to any disclaimer, the term of this patent is extended or adjusted under 35 U.S.C. 154(b) by 930 days.

(21) Appl. No.: 17/946,934

(22) Filed: Sep. 16, 2022

(65) Prior Publication Data

US 2023/0076929 A1 Mar. 9, 2023

Related U.S. Application Data

(63) Continuation of application No. PCT/US2021/023277, filed on Mar. 19, 2021.
(Continued)

(51) Int. Cl.
*A61F 2/12* (2006.01)
*A61F 2/00* (2006.01)
(Continued)

(52) U.S. Cl.
CPC .............. *A61F 2/12* (2013.01); *A61F 2/0077* (2013.01); *A61F 2/24* (2013.01); *A61F 2/2846* (2013.01);
(Continued)

(58) Field of Classification Search
CPC .. A61F 2/12; A61F 2/0077; A61F 2210/0004; A61F 2240/002
See application file for complete search history.

(56) References Cited

U.S. PATENT DOCUMENTS

| | | | |
|---|---|---|---|
| 6,702,858 | B2 | 3/2004 | Zilla et al. |
| 7,371,400 | B2 | 5/2008 | Borenstein et al. |

(Continued)

FOREIGN PATENT DOCUMENTS

| | | |
|---|---|---|
| CN | 109172044 A | 1/2019 |
| EP | 2995278 A1 | 7/2018 |

(Continued)

OTHER PUBLICATIONS

International Search Report with Written Opinion, issued in corresponding PCT Application No. PCT/US2021/023277, dated Oct. 7, 2021, two-hundred and fifty-seven (257) pages.
(Continued)

*Primary Examiner* — Bruce E Snow
(74) *Attorney, Agent, or Firm* — Dinsmore & Shohl LLP

(57) ABSTRACT

Certain aspects of the present disclosure provide a flexible scaffold implant comprising a plurality of layered structures, the plurality of layered structures comprising: a first layered structure having a three-dimensional (3D) shape and formed from a bioresorbable material, and a second layered structure conforming to the corresponding 3D shape of the first layered structure and formed from the bioresorbable material. The first layered structure is arranged in proximity to the second layered structure. The first layered structure is configured to dissolve for resorption at a different rate than the second layered structure based on design elements of the first layered structure and the second layered structure. The plurality of layered structures are flexible.

16 Claims, 26 Drawing Sheets

235

Related U.S. Application Data

(60) Provisional application No. 62/991,810, filed on Mar. 19, 2020.

(51) Int. Cl.
| | | |
|---|---|---|
| *A61F 2/24* | (2006.01) | |
| *A61F 2/28* | (2006.01) | |
| *B33Y 80/00* | (2015.01) | |

(52) U.S. Cl.
CPC ....... *B33Y 80/00* (2014.12); *A61F 2002/0086* (2013.01); *A61F 2210/0004* (2013.01); *A61F 2250/0098* (2013.01)

(56) References Cited

U.S. PATENT DOCUMENTS

| | | | | |
|---|---|---|---|---|
| 11,564,792 | B2 * | 1/2023 | Zopf | ......................... A61F 2/18 |
| 2016/0199538 | A1 | 7/2016 | Schussler | |
| 2017/0304492 | A1 | 10/2017 | Iwai et al. | |
| 2017/0354521 | A1 * | 12/2017 | Ryan | ...................... A61F 2/915 |
| 2019/0133653 | A1 | 5/2019 | Swarts | |
| 2019/0151081 | A1 | 5/2019 | Limem et al. | |
| 2024/0216122 | A1 * | 7/2024 | Limem | ................... A61L 27/48 |

FOREIGN PATENT DOCUMENTS

| | | |
|---|---|---|
| WO | 2018130949 A1 | 7/2018 |
| WO | 2019217335 A1 | 11/2019 |

OTHER PUBLICATIONS

International Preliminary Report on Patentability issued in corresponding PCT Application No. PCT/US2021/023277, dated Sep. 20, 2022, twenty (20) pages.

Xue et al., www.promega.com/CustomManufacturing, "Osteochondral tissue coculture: An in vitro and in silico approach", Jan. 23, 2019, thirteen (13) pages.

Bandyopadhyay et al., "Additive manufacturing of multi-material structures", Mar. 27, 2018, sixteen (16) pages.

Kong et al., Acta Biomaterialia, "Bo-engineeing a tissue flap utilizing a porous scaffold incoprating a human induced pluripotent stem cell-derive endothelial cell capillary network connected to a vascular pedicle", Oct. 31, 2018, fourteen (14) pages.

* cited by examiner

220

225

230

235

240

245

250

255

260

265

600

602

604

700

710

720

730

740

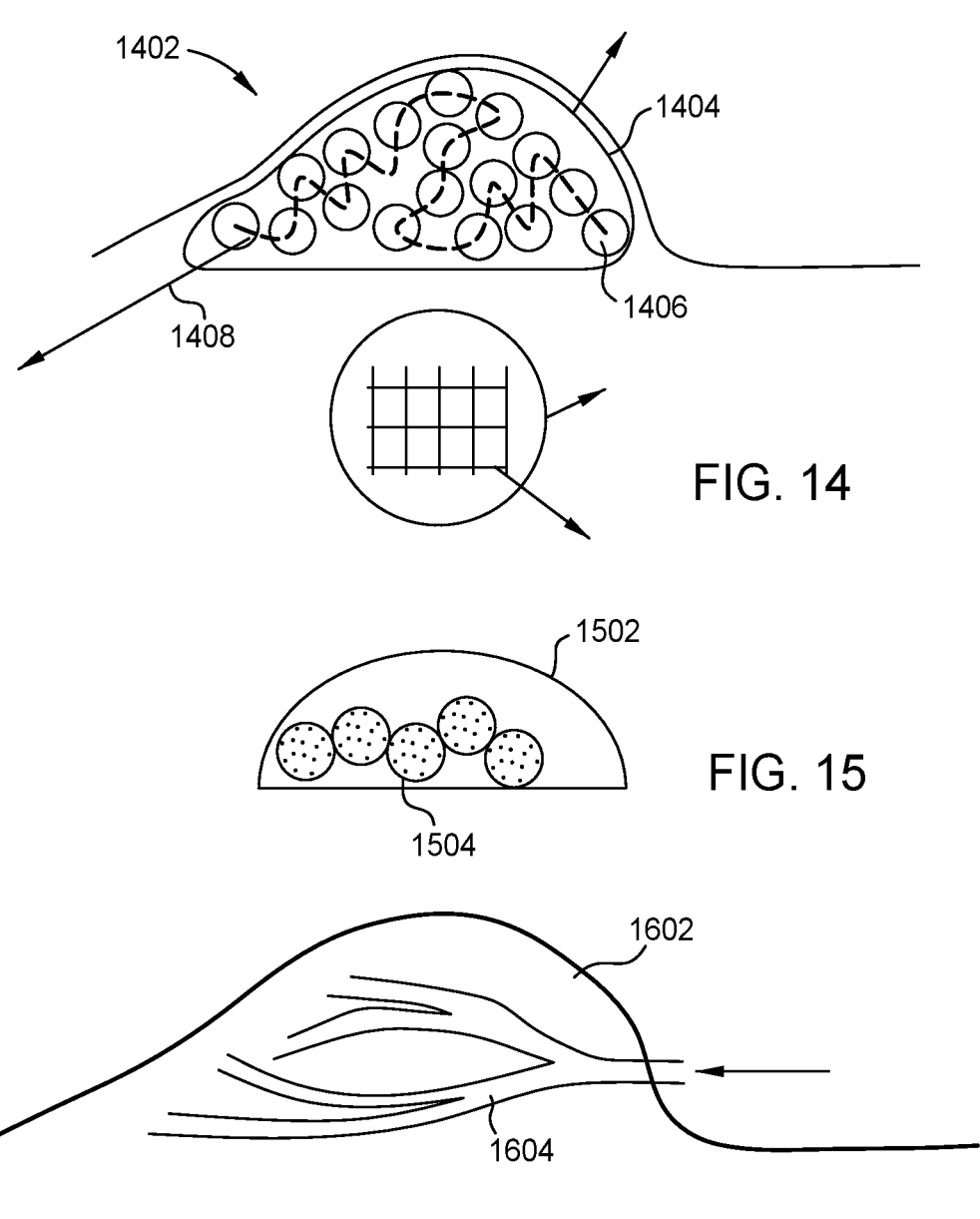
FIG. 14
FIG. 15
FIG. 16
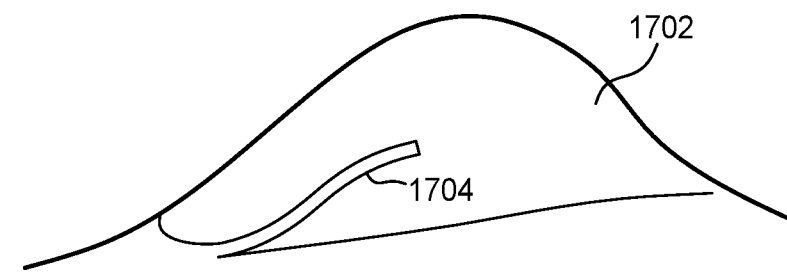
FIG. 17

2002

2004

2004

2004

2002

2002

2006

2006

SCAFFOLD BASED IMPLANTS

CROSS-REFERENCE TO RELATED APPLICATIONS

The present application is a continuation of International Application No. PCT/US2021/023277, filed Mar. 19, 2021, which claims the benefit of and priority to U.S. Provisional Application No. 62/991,810, entitled "Scaffold Based Implants for Breast Reconstruction" and filed on Mar. 19, 2020, the entirety of each of which is incorporated by reference herein for all purposes.

INTRODUCTION

Aspects of the present disclosure relate to systems and methods for constructing and/or employing implants and, in particular, 3D biodegradable scaffolds for tissue regeneration and reconstruction.

Various medical procedures employ implants (such as scaffold-based implants) surgically inserted into a patient's body to aid in reconstruction of an aspect or portion of the patient's body. The implant may be used to replace, support, and/or augment a biological structure in the patient's body. For example, cancer, such as breast cancer, may have many treatments, including surgical options, such as mastectomies, lumpectomies, and the like. Such surgical options may include implants for reconstructive purposes. However, results of the surgical options may be structurally, medically, aesthetically, and/or psychologically unsatisfactory to the patient and/or a medical professional. For example, the implant may not adhere properly to tissue in the patient's body or may be uncomfortable for the patient.

Therefore, there is a need for improved implants, and more specifically, implants, for use in such surgical and/or reconstructive procedures, which lead to improved surgical outcomes for patients.

BRIEF SUMMARY

Certain embodiments provide a flexible scaffold implant comprising a plurality of layered structures, the plurality of layered structures comprising a first layered structure having a three-dimensional (3D) shape and formed from a bioresorbable material and a second layered structure conforming to the corresponding 3D shape of the first layered structure and formed from the bioresorbable material. The first layered structure is arranged in proximity to the second layered structure. The first layered structure is configured to dissolve for resorption at a different rate than the second layered structure based on design elements of the first layered structure and the second layered structure. The plurality of layered structures are flexible.

Another embodiment provides a method of manufacturing the scaffold implant.

Another embodiment provides a method of regenerating tissue using the scaffold implant.

Other embodiments provide processing systems configured to perform the aforementioned methods as well as those described herein; non-transitory, computer-readable media comprising instructions that, when executed by one or more processors of a processing system, cause the processing system to perform the aforementioned methods as well as those described herein; a computer program product embodied on a computer readable storage medium comprising code for performing the aforementioned methods as well as those further described herein; and a processing system comprising means for performing the aforementioned methods as well as those further described herein.

The following description and the related drawings set forth in detail certain illustrative features of one or more embodiments.

BRIEF DESCRIPTION OF THE DRAWINGS

The appended figures depict certain aspects of the one or more embodiments and are therefore not to be considered limiting of the scope of this disclosure.

FIG. 14 shows a scaffold implant comprising a flexible outer shell surrounding a plurality of spherical chambers, in accordance with exemplary embodiments.

FIG. 15 depicts a scaffold implant comprising a plurality of spherical structures comprising colony forming units (CFUs) deposited therein, in accordance with exemplary embodiments.

FIG. 16 depicts a scaffold implant comprising one or more additional branch-like structures, in accordance with exemplary embodiments.

FIG. 17 depicts a scaffold implant having one or more elements for receiving one or more blood vessels and/or cells, in accordance with exemplary embodiments.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1A:
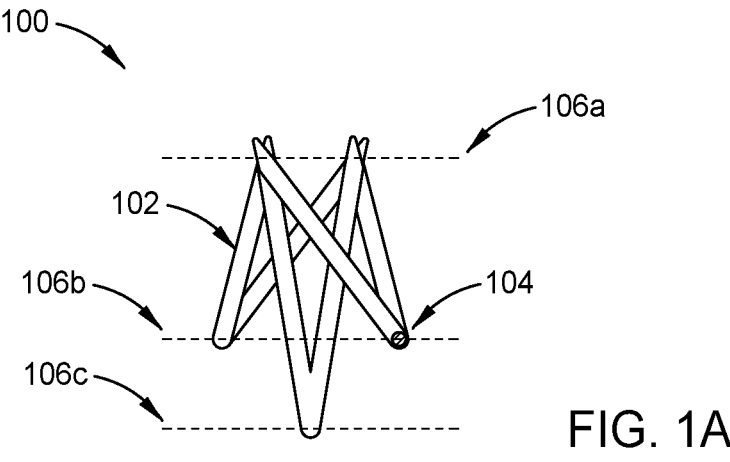
FIG. 1A depicts a representation of a 3-dimensional (3D) structure of an element that forms the scaffold implant described herein, in accordance with exemplary embodiments.

Aspects of the present disclosure provide improved implant apparatuses, devices and methods for using the improved implants in surgical procedures to treat conditions arising from trauma, tumors, congenital deformities, and the like. In various examples described herein, the surgical procedures involve reconstructive surgery or tissue regeneration (among other types of surgery) for one or more patient body parts, organs, tissue, joint and the like. More specifically, the apparatuses, devices and methods described herein involve scaffold-type implants that provide improved adherence to tissue in the patient's body, improved structural support for new tissue regeneration and reconstruction in the patient's body, improved acceptance of the implant by the patient's body, and improved quality of life for the patient.

Existing reconstruction and regeneration solutions include synthetic (for example, silicon-based) implants, tissue expanders, fat transfer (for example, lipotransfer), and the like. However, each of these solutions may present complications or have negative side effects. For example, fibrous capsules may form around the silicon-based implants and fat transfer solutions may suffer from loss of transferred fat or calcification over time, which may require multiple surgeries to complete or correct. Furthermore, such reconstruction solutions may cause soft tissue irritation and result in an undesirable reconstructive appearance due to the procedure and/or corresponding implants.

Various stem cell options may exist for use in tissue regeneration of a number of tissues and tissue types, such as embryonic stem cells, differentiated cell lineages, induced pluripotent stem cells (iPSCs), and mature cells. In corresponding regeneration procedures, the stem cells used for the tissue regeneration may be selected based on the tissue to be regenerated. For example, mesenchymal stem cells (MSCs) may be used to regenerate chondrocytes, osteocytes, bone tissue, and so forth, while cardiac stem cells are used to regenerate cardiac tissue, adipocytes to regenerate adipose tissue, and so forth. However, while tissue regeneration therapies involving stem cells do provide successful outcomes, such procedures face many hurdles, including tissue complexities, costs of treatment, need for additional hormone therapy, successful post clinical trial implementation, and the like.

Adipose tissue, or fat, is generally available in abundance in a patient. As described herein, adipose tissue (and various other tissue types) can be an option for tissue regeneration and reconstruction procedures. For example, in post-mastectomy breast reconstruction procedures, adipose tissue can be used to fill a missing soft tissue volume (for example, where soft tissue was removed or excised) and to recreate the physical appearance of the breast. Standard, one-size-fits-all implant constructs may enable recreation or reconstruction of breast tissue. However, such standard constructs may not be ideal for all patients because different patients (and, thus, different breast reconstructions procedures) have different requirements and issues (physical and otherwise) based on numerous characteristics. Such characteristics may include patient age, volume to be filled in the patient, characteristics of any corresponding tumor (such as size, location, and nature of the tumor, and so forth).

Adipocytes may make up a majority of the adipose tissue volume. The adipocytes include cytoplasm that contains lipid droplets, which give the adipocytes a spherical shape, though the shape of the adipocytes may vary during different stages of stem cell differentiation. Apart from the adipocytes, adipose-derived stem cells (ASCs), endothelial cells, mural cells, extra cellular matrix (ECM), and others also compose the adipose tissue. Natural ECM constituting of stromal and basement membranes may provide mechanical support for the adipocytes. Each adipocyte can be found in proximity with a capillary, such that angiogenesis and adipogenesis cycles can be synchronized.

The ASCs may have a high proliferative capacity and can differentiate into multiple cell lineages—osteogenic, chondrogenic, and adipogenic. The fate of the ASCs may be regulated by chemical and mechanical factors, where the mechanical factors are potent in-vitro even in the absence of chemical factors. Thus, it is important to direct cellular differentiation of the ASCs towards the desired lineage, such as breast tissue, in consideration of the mechanical factors. In some embodiments, such factors may be considered when selecting implant materials and structure, as discussed in more detail below.

In some instances, mechanical properties of a substrate or material forming the scaffold implant may play a role in guiding stem cell differentiation (for example, guiding the differentiation of the ASCs). For example, adipogenic differentiation and osteogenic differentiation of stem cells are inclined to occur on a substrate with a stiffness similar to in vivo microenvironments of the stem cells. For example, substrates that mimic the native stiffness of adipose tissue promote adipogenic marker upregulations and adipogenesis. On the other hand, excessive stresses and strains might prevent the differentiation of stem cells into adipocytes. Thus, the substrate stiffness considerations may also be applied to selecting implant materials and structures.

In many circumstances, the reconstructive surgery and tissue regeneration procedures involve different types of tissues in the same procedure. For example, native breast tissue is not homogenous, comprising a mammary gland that may be centrally located and adipose tissue that generally surrounds the glandular tissue. Each of these tissues may have its own characteristics, such as tensile and elastic properties, mechanical support(s), and so forth. With regard to breast reconstruction, the goal is to restore a patient's breast volume with adipose tissue, preferably autologous, while maintaining tactile sensation of the reconstructed breast and keeping calcification and other complications to a minimum or reduced. The tensile and elastic characteristics of the breast are produced by three major factors: 1) an amount and quality of fat in the breast, 2) an amount and quality of glandular and duct tissue in the breast, and 3) the mechanical characteristics of fibrous support structures of the breast. In some cases of breast reconstruction, the scaffold implant may be used to restructure multiple types of tissue, for example the glandular tissue and the fat tissue. Alternatively, even when an implant site natively comprises different types of tissue, the scaffold implant is used to implant a single type of tissue. For example, in the breast reconstruction described herein, the glandular tissue may not be reconstructed, as the glandular tissue may be associated with heightened cancer risk. Thus, characteristics of the native tissue itself may be factors for selecting materials, structure, and/or other characteristics of the scaffold implant to ensure that the regenerated or augmented tissue from the scaffold implant is as similar as possible to the native tissue.

Scaffold implants, preferably biodegradable scaffold implants, may act as synthetic substrates similar to natural ECM and provide the structural support for tissue regeneration of varying types of tissues. Existing implants used for tissue regeneration experience various shortcomings, including clustered and/or limited cell attachment and proliferation, surface isolated growth of cells (for example, growth observed only on the surface of the implant), and little to no cell migration towards an interior of the implant, which may lead to cell cluster formation, necrosis, and calcification. Additionally, existing bioresorbable implants may fail to provide adequate structural and biological support for tissue regeneration. Furthermore, such existing implants may be resorbed by the patient's body before new tissue cells implanted with or for use with the bioresorbable implants have adequate opportunity to create vascular connections and/or be seeded. Thus, the existing implants can result in an overall fat volume loss, for example, observed in cases of lipotransfer.

In some embodiments, the scaffold implant described herein created from one or more bioresorbable materials may aim to support transition between different phases of tissue regeneration during a tissue growth cycle, such as from harvesting tissue from a donor site for injection at one or more recipient sites. The tissue, during the growth cycle, may transition from few injected cells to fully matured and regenerated tissue at the recipient site.

An ideal implant may mimic the native environment of the tissue for the implant to improve chances of the implant successfully generating an adequate amount of tissue to fill a volume of an implant site of the patient's body. The success of the implant may be defined by an amount of tissue regenerated in relation to the volume being filled, the comfort of the patient, a visual appearance of the implant site, a function of the implant site, a feel of the implant site, and the like. In the case of the breast reconstruction example introduced above, the ideal implant may mimic a microenvironment of the breast while compensating for the tissue(s) and corresponding properties that may be missing (in other words, excised or removed), such as the glandular tissue.

In some embodiments, the apparatuses, devices and methods described herein disclose scaffold implant and corresponding designs that mimic native tissue characteristics such that the reconstructed or restored tissue regenerated by or with the scaffold implants functions and/or is similarly structured to the native tissue being replaced. Such scaffold implants as described herein may better restore tissue volumes, tissue functions, and/or the like as compared to previous or existing implants. For example, the disclosed scaffold implant designs may improve vascularization and lipofilling, improve maintenance of the deposited tissue volume by preventing fat tissue absorption, reduce mechanical load on the deposited new (and surrounding native) tissue to promote tissue growth, promote adequate and desired cell growth, and/or enhance attachment of the scaffold implant and new tissue to the surrounding native tissue.

In some embodiments, the disclosed scaffold implants and corresponding designs may be compressible to make any reconstruction and/or regeneration implant procedures less invasive as compared to existing implants and procedures. The disclosed scaffold implant may also be biodegradable and have biomimetic mechanical properties that promote the tissue regrowth, such as flexibility of and support by the scaffold implant. Such characteristics of the scaffold implant may reduce the strain and stress of the scaffold implant on the patient's body and reduce the stress on the new tissue regenerated on the scaffold implant.

As described in more detail below, in certain embodiments, the disclosed scaffold implants and designs comprise a three-dimensional scaffold structure as a support structure for the tissue reconstruction or regeneration. The scaffold implant may comprise micro and/or macroscopic elements that help mimic a biological microenvironment of the native tissue to be regenerated. Mechanical properties such as elasticity, flexibility, stiffness, etc., may be properties attributed by the material used to create the scaffold implant and/or scaffold structures thereof. In some embodiments, the scaffold implant may be formed of relatively low stiffness material or relatively high stiffness material. In certain embodiments, the design of the scaffold implant and/or the elements thereof affect the mechanical properties such as the flexibility of the device. In other words, a scaffold implant may have a relatively high flexibility despite being made of a material that has a high stiffness, because the design creates flexibility of the scaffold implant despite the material from which it is made, and vice versa. In some embodiments, the flexibility of the scaffold implant may lend advantages such as: to improve adipogenesis by mimicking low stiffness of adipose tissue, to mimic tactile sensation, to avoid the material is working beyond the elastic limit, to allow to return to an initial un-deformed shape once the stress is released from the device, to avoid deformation or breakage, to resist contraction forces after radiotherapy with limited complications, and/or the like.

Apart from the scaffold implant mimicking the biological microenvironment of the native tissue, the mechanical properties of the scaffold implant can affect its biological performance by changing the processes of cellular adhesion, proliferation, differentiation, and extracellular matrix deposition. For example, the stiffness (and/or other mechanical properties) of the scaffold implant could be molded to match the native tissue to guide the differentiation of seeded cells and restore the function of the reconstructed tissues. This may be obtained by appropriately selecting proper materials for the scaffold implant and/or tuning the scaffold implant to implement to desired mechanical properties, for example, to mimic the native tissue.

The micro and/or macroscopic elements may comprise a structure composed of one or more of a gradient of pores and/or cavities, mesh, sponge, tubular structures, struts, and/or the like to support seeded cells or tissue during different stages of a cell or tissue cycle, and so forth. As such, in some embodiments, the micro and/or macroscopic elements are composed in a plurality of layers that form the structure of the scaffold implant. Furthermore, in some embodiments, the 3D scaffold implant may comprise one or more pores, one or more of channels, one or more of spheres, one or more of struts, one or more columns, one or more rods, one or more beams, one or more wires, one or more of annuli, one or more of ovoids, one or more of spheroids, one or more of oblate spheroids, one or more of threads, one or more of rounded triangular prisms, or a combination of one or more hybrid structural elements, depending on the type of tissue to be regenerated.

In some embodiments, the implants described herein employ spatial characteristics of various components to influence and/or guide the cellular differentiation of deposited cells into different cell lineages by mimicking the microenvironment of the native tissue. For example, the mechanical structure and the material used for the scaffold implant described herein may promote differentiation into adipogenic lineage. In some instances, chemical factors, such as growth factors, may be incorporated into/or on the scaffold implant or the procedure itself to support or promote cell proliferation and/or differentiation.

In some instances, the bio mimicking characteristics (for example, the mimicking of the biological microenvironment of the native tissue) of the scaffold implant may be a result of the material used to form the scaffold implant. Forming the scaffold implant of bioresorbable material(s) may be preferable because such materials are biocompatible and resorb into the patient's body over time and, thus, subsequent surgeries or procedures to remove the scaffold implant are not required for such scaffold implants.

In certain embodiments, the scaffold design of the scaffold implant is patient specific, such as to match aspects of the patient's body. For example, there may be substantial variability in the anatomy, size, shape, consistency, elasticity, fat distribution, and so forth, of patient tissue, such as breast tissue between patients. In the case of breast tissue, one or more of these aspects may differ in people of different ages. As the result also has to be aesthetically pleasing, individual characteristics and/or preferences may also need to be taken into account at the time of tissue reconstruction. These factors may be addressed by making the scaffold-based implant patient-specific.

In certain embodiments, the patient specific scaffold implant may be generated using various technologies. For example, imaging modalities such as CT scans, MRI, ultrasounds, optical scanning, and the like, may be used to create a digital capture of/image the shape of a tissue site of a patient. The shape of the scaffold implant may then be designed to be patient-specific (e.g., conform to the anatomy of the patient) based on the imaging. In some embodiments, other systems, such as augmented reality, may be used to create a digital profile of the patient in combination with existing imaging modalities. Using the available technology and information, a tissue density profile may be created for each patient, based on which the patient-specific scaffold implant is created. Thus, the scaffold implants may also vary in one or more of size, shape, microscopic elements, and macroscopic elements of the scaffold implants in accordance with the patient profile and/or the treatment offered.

Furthermore, the scaffold implant may be printed using additive manufacturing techniques. The additive manufacturing techniques (for example, 3D printing techniques or technology) may comprise a powder based fusion or melting approach (for example, Selective Laser Sintering, Selective Laser Melting, Binder Jetting, and the like), a filament or pellet-based extrusion or jetting approach (for example, Fused Deposition Modelling), a liquid based approach (for example, Vat Polymerization, Melt Electro Writing, Melt Electrospinning, Direct Polymer Melt Deposition, Direct-Write Electrospinning, and the like), and/or a combination thereof. Such additive manufacturing techniques may enable the scaffold implant to be constructed in a plurality of layers, which may improve flexibility of the scaffold implant.

In addition to the breast reconstruction examples described above, the scaffold implants described herein may similarly be used for other similar implants, such as soft-tissue reconstruction and/or regeneration procedures where flexibility of the scaffold implants is desirable. For example, the scaffold implants described herein may be used in cosmetic surgeries (such as rhinoplasty, facial rejuvenation, anaplastology, and the like), organ reconstruction (such as liver, cardiac, skin, penile, and the like), vascular procedures, dental procedures (such as gum grafting), joint procedures (such as replacement or repair of ligaments, meniscus, and the like) or cardiac procedures (such as for patches).

For example, the scaffold implant may be designed to replace and/or completely or partially fill a myocardial defect. The internal structure of the corresponding scaffold implant may comprise one or more macroscopic and/or microscopic elements (also referred to herein as macro/ microstructures, respectively) that may be modified to mimic native myocardial tissue. For example, the scaffold implant may be coated with extracellular matrix proteins, substrates, and/or growth factors to allow cardiomyocyte attachment and proliferation. Furthermore, the scaffold implant may be pre-vascularized and loaded with stem cells, progenitor cells, cardiomyocytes, fibroblasts, endothelial cells, and/or a combination thereof. In such soft tissue procedures, the scaffold implant may be used for one or more of soft tissue reconstruction, augmentation, regeneration, correction, and/or reduction procedures. The scaffold implant may also be used in excision biopsy procedures.

Additionally, the scaffold implants described herein may be employed in non-soft-tissue reconstruction or regeneration procedures, such as those requiring spacers or grafts in distraction or osteotomy procedures for bony tissue, fusion devices (spine), cartilage defect repair procedures, and/or the like. For example, the scaffold implant may act as a replacement for bone grafting by designing the shape of the scaffold implant structure to fit in a bone defect or provide a support structure along with a bone implant. Thus, the scaffold implant may compensate for bone and/or tissue damage and/or loss during accident and/or surgery. For example, the scaffold implant may be employed during joint replacement surgeries, such as total knee arthroplasty, partial knee arthroplasty, hip replacement surgeries, shoulder surgeries, craniomaxillofacial surgeries, cartilage and/or ligament tear surgeries, and the like. The microstructure of the scaffold implant may be modified to mimic the properties of bone. Furthermore, the mechanical characteristics may be modified to make the scaffold implant weight bearing. The scaffold implant may further be loaded with growth factors and/or cells that have the capability to develop into mature bone cells.

Example Scaffold Implant Components

As described herein, the scaffold implant may be formed from a number of smaller components or elements arranged in a structure corresponding to the desired scaffold implant shape and/or size. Details of these smaller elements are provided below.

FIG. 1A depicts a representation of a 3-dimensional (3D) structure of an element 100 that forms the scaffold implant described herein. The element 100 comprises a plurality of struts or beams 102 (referred to herein interchangeably as "struts") and a number of nodes 104 at which two or more of the struts 102 are connected to each other. In some embodiments, the nodes 104 may enable movement of the struts 102 relative to one another and the nodes 104, while the struts 102 may provide support between two coupled nodes 104. As shown, the struts 102 and the nodes 104 are arranged and connected such that the components of the element 100 create three layers 106a-c. As shown, the nodes 104 on the layer 106a are connected to one or more nodes 104 on layer 106b with struts 102. The nodes 104 on the layer 106a are also connected to one or more nodes 104 on layer 106c. In some embodiments, the struts 102 may connect different combinations of nodes 104 on different layers 106.

As shown, the struts 102 may be substantially straight segments of material between two nodes 104. However, in some embodiments, the struts 102 may comprise curved segments or segments of other shapes (or a combination thereof) while connecting the two nodes 104. In some embodiments, the struts 102 may be formed from a particular material based on the characteristics or parameters of the material, as they would relate to the tissue being reconstructed and/or regenerated. In some embodiments, the struts 102 may be rigid, flexible, or porous. In some embodiments, the struts 102 are beams, are hollow, or comprise one or more internal or external channels. The struts 102 may connect nodes 104 distributed on the same layer or on different layers within the element 100 such that the connection between the nodes 104 forms one element 100. The struts 102 may connect nodes 104 distributed on different layers within the element 100 such that the connection between the nodes 104 forms one element 100. In some embodiments, the struts 102 may connect nodes 104 from neighboring elements 100. Furthermore, the struts 102 may have a constant diameter or thickness, cross-sectional shape, linear relationship, and the like, along the multiple layers. In certain embodiments, the struts 102 can present a spatial gradient of their thickness, for example, varying their thickness according to the different layers or along the same layer. In certain embodiments, the struts 102 of the element 100 may be hollow or of an appropriate structure that enable the struts 102 to act as an anchor for the element 100 (and/or the scaffold implant) to the surrounding native tissue when implanted. This may help keep the element 100 and, thus, the scaffold implant in place within the surrounding tissue.

The nodes 104 may enable movement of the struts 102 connected at each node 104 in one or more directions. For example, the node 104 may allow rotation or pivoting of the struts 102 coupled at the node 104 around an axis while limiting movement of the struts 102 in a direction along the axis. By enabling such rotation or pivoting, the nodes 104, in combination with the struts 102, enable the element 100 to be flexible in response to forces exerted on the element 100. For example, when the element 100 is compressed vertically (for example, downward with respect to the page of FIG. 1A), the nodes 104 may enable the struts 102 to move in two-dimensions (for example, in a plane of the page of FIG. 1A) but restrict movement in the third dimension (for example, into or out of the page). In some embodiments, the struts 102 may comprise a flexible material that enables the struts 102 to absorb certain forces to which the scaffold implant is exposed.

The element 100, as shown, comprises six (6) struts 102 and five (5) nodes 104. The struts 102 and the nodes 104 are arranged such that a top two nodes 104 (relative to a vertical orientation of FIG. 1A) create or are disposed in a first layer 106a, two middle nodes 104 create or are disposed in a second layer 106b, and a bottom node 104 creates or is disposed in a third layer 106c. The element 100 may absorb force such that any downward force exerted onto the element 100 is distributed to the struts 102 and the nodes 104, where the nodes 104 enable the struts 102 to pivot relative to one another to compensate for the downward force exerted onto the element 100. In some embodiments, the element 100 may convey any absorbed force to other elements 100 of the scaffold implant and/or to the surrounding native tissue. For example, when force is received in a given direction at a first element 100, the force may be conveyed to a second element 100 coupled to the first element 100 in the same direction as the force (also referred to as an opposing element), thereby opposing the force.

In some embodiments, the scaffold implant formed from the elements 100 may comprise a 3D structure comprising a plurality of layers 106a-c. Each layer 106a-c of the element 100 (and, thus, the scaffold implant) may comprise one or more of the macro and/or microscopic elements described herein. In some embodiments, the plurality of layers 106a-c creates a repetition of the macro and/or microscopic elements. Furthermore, each layer 106a-c may comprise one or more nodes 104. The layers 106a-c of the element 100 may create multiple layers in the scaffold implant formed from the plurality of elements 100. In some embodiments, the elements 100 may be arranged in various arrangements to create a specific or desired shape, configuration, volume, and so forth for a particular implant site.

Figure 1B:
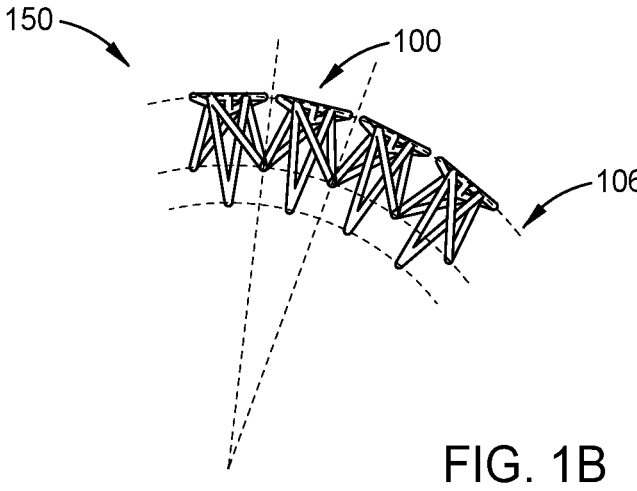
FIGS. 1B and 1C depict variations of the element of FIG. 1A arranged to form a partial arrangement of one or more layers of a scaffold implant, where neighboring elements are connected at nodes in one or more layers, in accordance with exemplary embodiments.
Figure 1C:
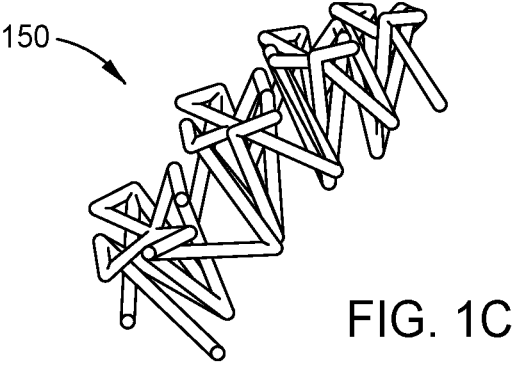

A plurality of the elements (for example, corresponding to the element 100) may be arranged to form the scaffold implant described herein. As such, the scaffold implant described herein may rely on the structural properties of the individual elements. For example, as shown in FIG. 1B, the elements can be arranged to form a partial arrangement 150 of the scaffold implant, where neighboring elements are connected at nodes in one or more layers. The elements are arranged such that the arrangement of the elements create an arc or semicircle representing a circular shape of the scaffold implant. FIG. 1C shows an alternate perspective of the partial arrangement 150 as shown in FIG. 1B of the elements.

The scaffold implant formed from the plurality of elements 100 may comprise various structural properties based on the design configuration and/or the material from which the plurality of elements 100 are formed. When the scaffold implant is employed in a tissue reconstruction, regeneration, or similar procedure, the scaffold implant may mimic the native tissue's microenvironment based on these properties. In some embodiments, a selection of which property(ies) of the native tissue are mimicked (or primarily mimicked) by the scaffold implant is determined based on the native tissue being mimicked. For example, when the scaffold implant is used with breast tissue, the flexibility of the scaffold implant may be of greatest importance and, thus, the material used for the scaffold implant for breast tissue applications may be selected to best mimic the flexibility of the native breast tissue. The other structural properties (for example, elastic properties, tensile properties, and the like) may be the property(ies) of greatest importance for different types of native tissues and, thus, the material (or other features of the scaffold implant) may be selected accordingly.

In certain embodiments, said other features may comprise of radiopaque markers. In certain embodiments, the scaffold-based implant may be created with (partially) radio-opaque materials. In some embodiments, the scaffold implant may be created with entirely radiolucent materials (in other words, materials that are transparent to X-rays, and the like) and enhance detection of recurrences of a condition before the scaffold implant is either removed or absorbed.

In certain embodiments, the plurality of elements 100 forming the scaffold implant can be arranged such that the scaffold implant has a shape that is substantially round or spherical, oblate, oval, dome-like, and so forth. In some instances, the shape of the scaffold implant depends on a volume of the native tissue being replaced in the patient's body. Alternatively, the shape of the scaffold implant may depend on one or more neighboring structures in the patient's body at a site where the native tissue is being replaced. In some instances, multiple layers of the plurality of elements 100 may be arranged to create multiple layers of elements 100 in the scaffold implant. In some embodiments, the scaffold implant may include a cavity or empty space at a center of the scaffold implant.

To create the 3D structure of the scaffold implant, the one or more layers 106a-c of the elements 100 may be aligned and distributed in order to be compliant with the external surface of the unit. In certain embodiments, the elements 100 are distributed or arranged to create the empty space inside the scaffold implant. The presence of the empty space may increase the flexibility of the scaffold implant. In some embodiments, the size of the empty space is dependent on the flexibility, support structure, and cell/tissue injection requirements. Multiple repetitions of the 3D-dimensional structure conformal to the surface are possible. For example, multiple elements 100 can be stacked on top of each other and entwined between layers or within layers. For example, two elements 100 on the same or different layers may be entwined. Furthermore, elements 100 within a layer may be conformal such that the elements have the same distance from a center point of the scaffold implant while being entwined with each other, such that the elements 100 may have starting points (for example, top or bottom nodes 104) on one or more layers (for example, a first element 100 may have its top node(s) 104 on the layer 106a and a neighboring element 100 may have its top node(s) 104 on the layer 106b, etc.

Figure 2A:
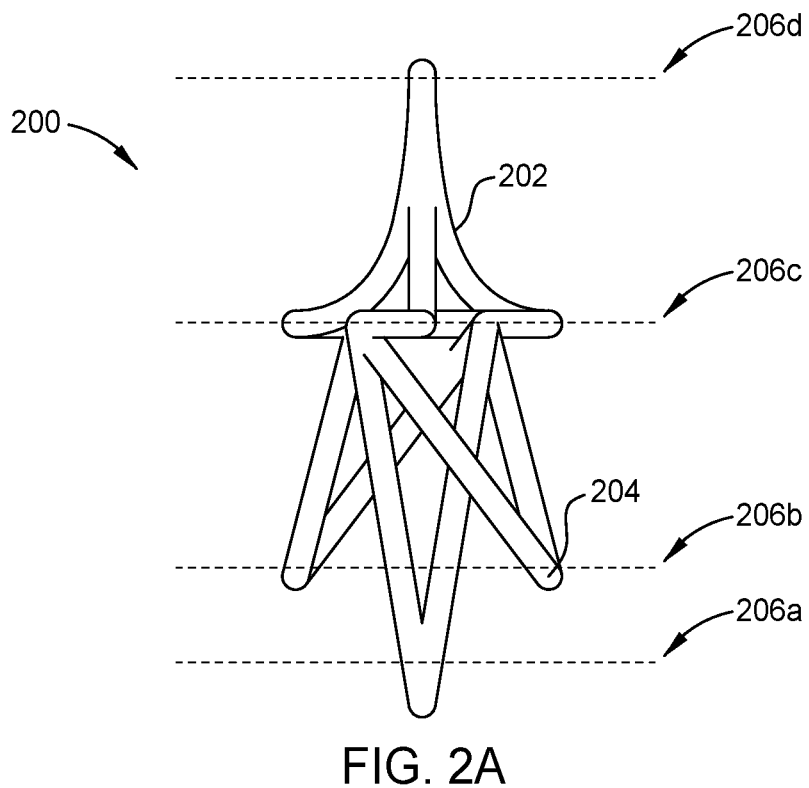
FIG. 2A depicts an example variation of an element of a scaffold implant having a plurality of projections extending from the elements forming the scaffold implant.

FIG. 2A depicts an example variation of an element 200 of a scaffold implant having a plurality of projections extending from the elements 200 forming the scaffold implant. The element 200 may comprise struts 202 (which may correspond to the struts 102) and nodes 204 (which may correspond to the nodes 104). Furthermore, the element 200 may comprise multiple layers 206a-d, which may correspond to features and aspects of the layers 106a-c. The element 200 may be formed by connecting multiple layers 206a-d of the struts 202 together using the nodes 204. The element 200 may be made taller than shown by adding one or more layers 206a-d of nodes 204 and struts 202 or shorter by removing one or more layers 206a-d of nodes 204 and struts 202.

The nodes 204 on layer 1 206a are connected to a number of nodes 204 on layer 3 206c by one or more struts 202. Within layer 3 206c, the nodes 204, which are connected to layer 1 206a, are also connected (for example, on the other side of the corresponding struts 202) to layer 2 206b nodes 204. These nodes 204 on layer 3 206c are also connected to other nodes 204 on the same layer 3 206c. The "other nodes" 204 on layer 3 206c are also connected to nodes 204 on layer 4 206d. In some embodiments, different combinations of layers 206a-d and nodes 204 are connected by the struts 202 based on, for example, a desired flexibility for the corresponding scaffold implant.

Thus, the struts 202 are entwined between the layers 206a-d of the element 200 using the nodes 204 and may give the element 200 the flexibility, which is necessary for the element 200 to behave as desired for the scaffold implant. For example, by entwining the nodes 204 using the struts 202 over the multiple layers 206a-d, the element 200 may have a balance within the element 200 itself. Thus, if a force is applied to the scaffold implant formed from these elements 200 (for example, the scaffold implant 220 shown in FIG. 2C), the force may be distributed throughout the scaffold implant. Thus, the elements 200 may give the scaffold implant its flexibility due, at least in part, to these entwined connections of struts 202 and nodes 204.

Thus, combining the elements 200 in the depicted architectures may create an overall shape that can withstand the forces generally experienced by implanted structures in different parts of the patient's body, such as breast tissue, which may require flexibility for adhesion of adipose cells.

In some instances, as described above with respect to the struts 102, the struts 202 connecting two nodes 204 can comprise a straight structure or portion, for example, as represented by the strut 202 connecting the nodes 204 of layer 1 206a and layer 2 206b. The struts 202 between the nodes 204 can also be curved, with the struts 202 between the nodes 204 for layer 3 206c and layer 4 206d. The curved struts 202 may have a different behavior and/or flexibility than the straight struts 202. By combining and arranging the struts 202 with variations of thickness, shape, density, stiffness, flexibility, and the like, in different combinations, the scaffold implant can be generated with desired mechanical properties, such as stiffness and/or flexibility. For example, the element 200, and further, the scaffold implant generated based on the elements 200, can have stiffness and/or flexibility properties that are customizable (along with the structure and arrangement of the elements 200).

Figure 2B:
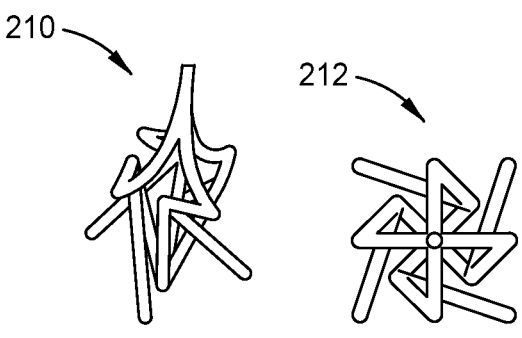
FIG. 2B shows different views of the element of FIG. 2A, including a perspective view and a vertical view, in accordance with exemplary embodiments.
Figure 2C:
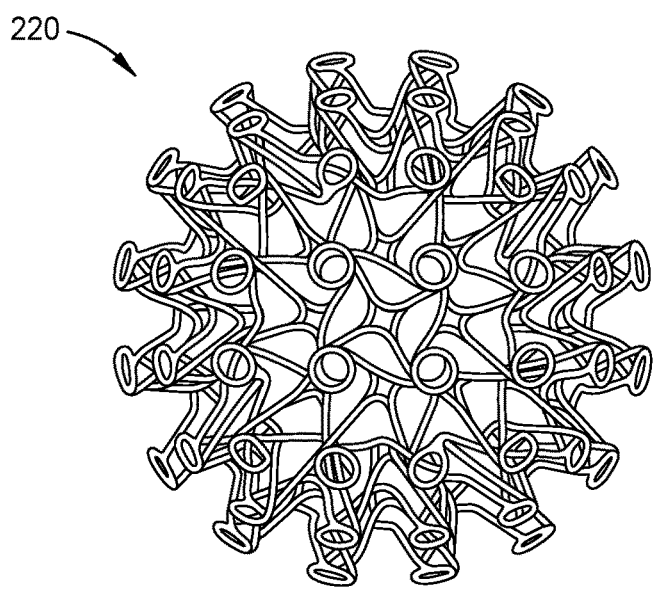
FIGS. 2C-2L depict various 3D scaffold implants generated based on a plurality of different types of elements, in accordance with exemplary embodiments.
Figure 2D:
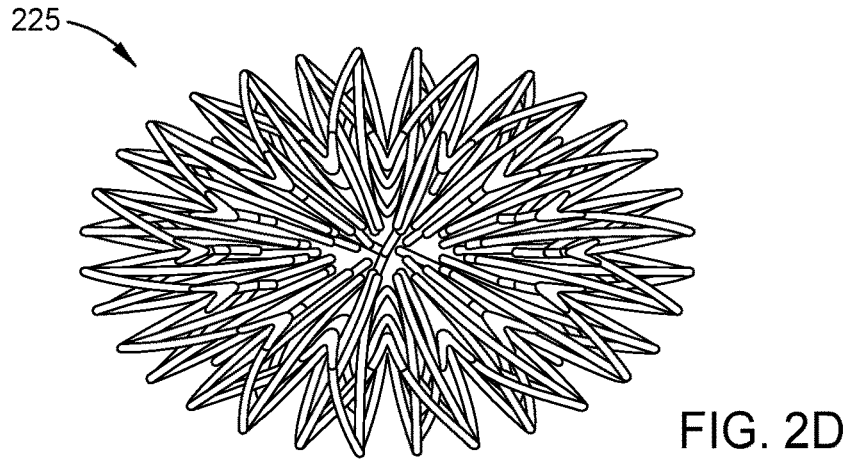
Figure 2E:
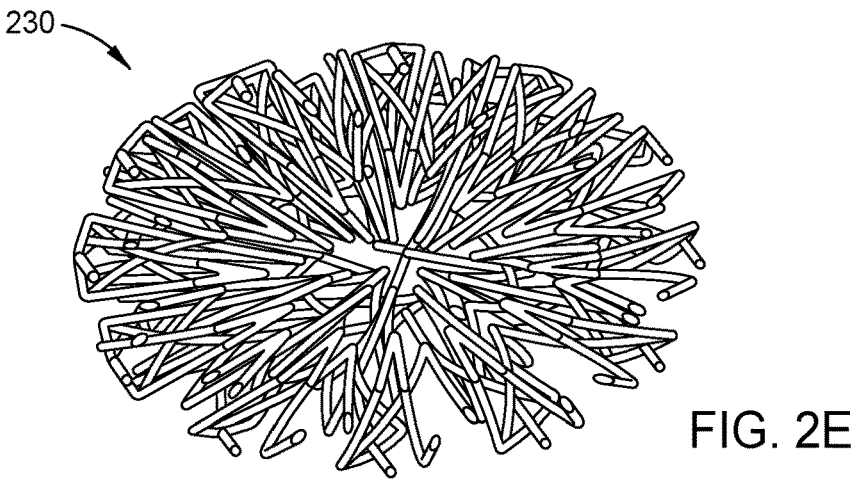
Figure 2F:
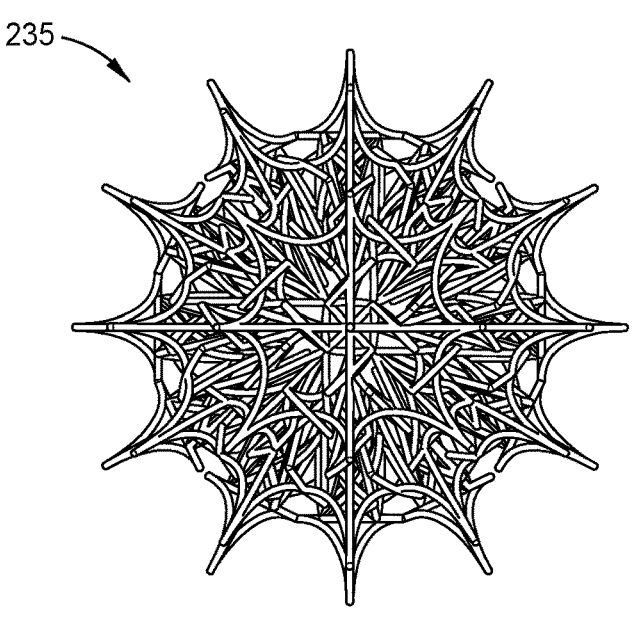
Figure 2G:
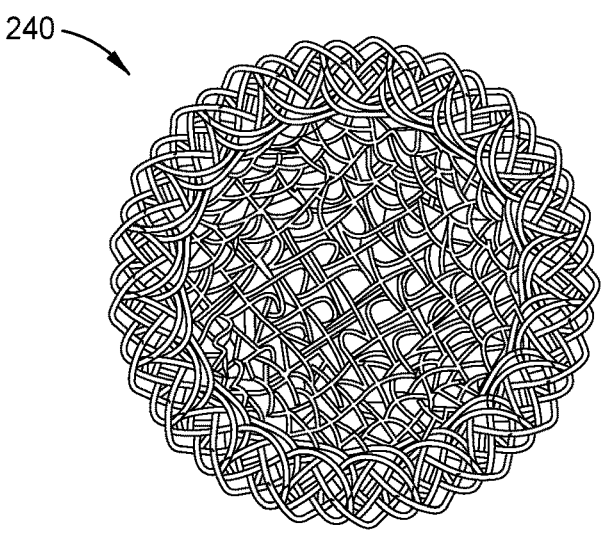
Figure 2H:
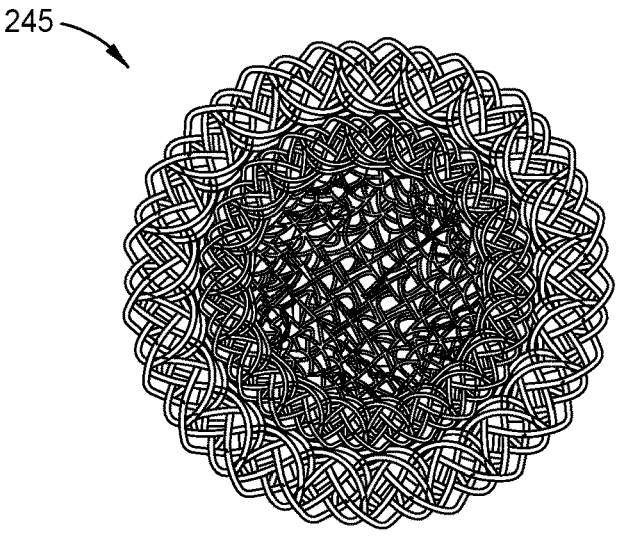
Figure 2I:
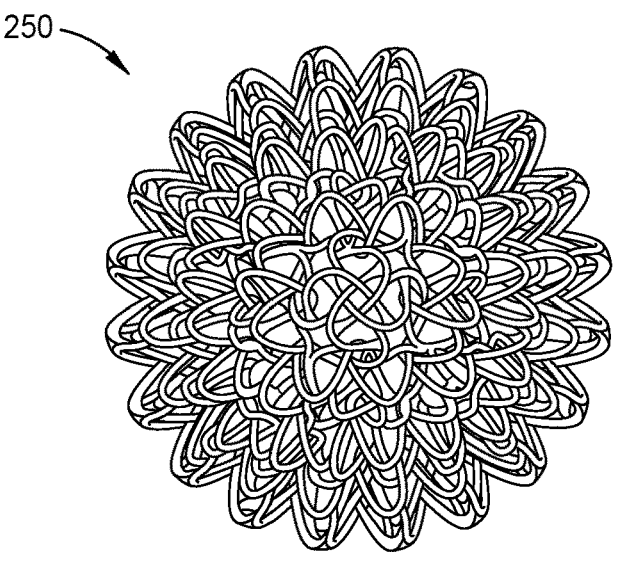
Figure 2J:
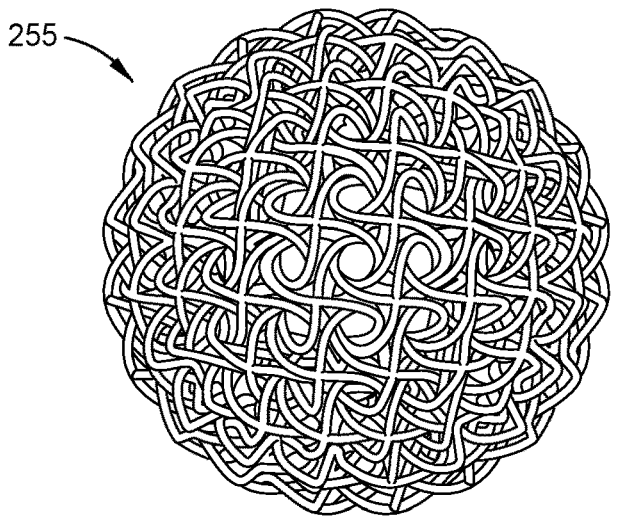
Figure 2K:
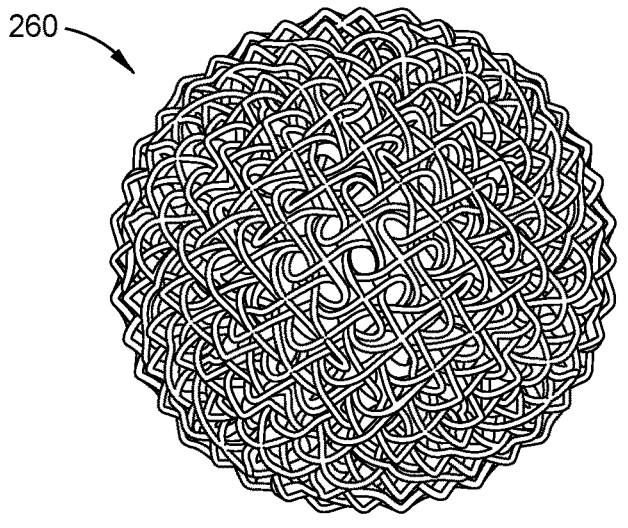
Figure 2L:
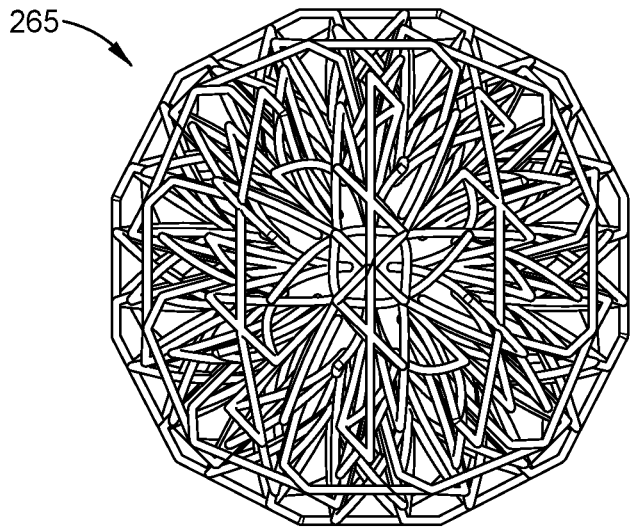

FIG. 2B shows different views of the element 200, including a perspective view 210 and a vertical view 212.

FIGS. 2C-2L depict various 3D scaffold implants 220-265 generated based on a plurality of different types of elements, for example the elements 100 and 200. Each of the scaffold implants 220-265 may have different physical and/or mechanical characteristics, such as different stiffnesses, flexibilities, behaviors, and the like. Different scaffold implants 220-265 may have different physical features based on, for example, variations between the scaffold implants 220-265, such as more pronounced protrusions (with varying densities), increased internal space or volume, different levels of stiffness and/or flexibility, and so forth. Thus, the different scaffold implants 220-265 may have different use cases and/or applications or be used in different locations in patients' bodies.

In certain embodiments, one or more of the scaffold implants 220-265 may have flexible properties that mimic the microenvironment of native surrounding breast tissue and may be implanted in patients that may have undergone a mastectomy or lumpectomy. Such applications may be of particular interest because currently few treatments exists which aim to restore the natural shape and feel of the breast for the patient or obtain a specific aesthetic outcome postoperatively. Furthermore, the scaffold implants 220-265 may maintain a stiffness akin to the soft tissues that they are replacing/generating while protecting the newly formed tissue from excessive stresses and strains, in part due to their complex designs. In certain embodiments the scaffold implants 220-265 may provide a mechanical framework supporting an overlying breast skin (or other skin, dependent on the implant site) envelope while maintaining the lost volume of tissue open for new tissue formation.

The scaffold implants (for example, one or more of the scaffold implants 220-265) may also promote tissue guidance by engaging in cell attachment, cell migration, cell proliferation, and/or cell differentiation (for example, adipogenesis and/or angiogenesis). In some embodiments, the microscopic elements of the scaffold implant are optimized to avoid coalescence of tissue, such as adipose tissue cells after lipofilling. To promote tissue regeneration and avoid fat loss, angiogenesis and/or adipogenesis may occur simultaneously. In certain embodiments, the scaffold implant (for example, one or more of scaffold implants 220-265) may be patient-specific. According to certain embodiments, the scaffold implant has a structure that promotes both angiogenesis and adipogenesis. In certain cases, such a hybrid design may permit use of pre-vascularized tissue, decellularised fat tissue, and/or ASCs deposited along with fat tissue or combinations thereof.

Example Scaffold Implant Details

Figures 3A, 3B:
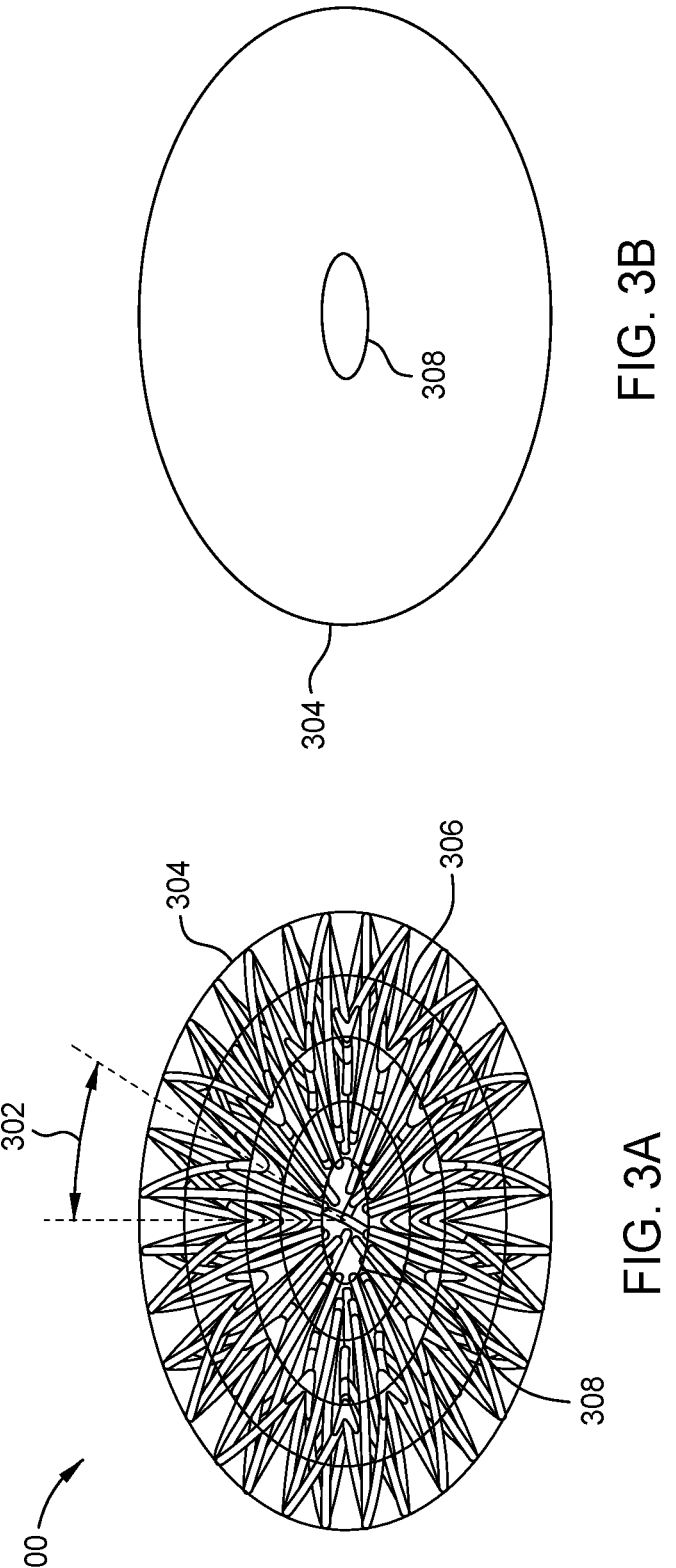
FIGS. 3A and 3B provide example representations of different aspects or portions of the scaffold implant formed from a plurality of elements as introduced above.

FIGS. 3A and 3B provide example representations of different aspects or portions of the scaffold implant 300 formed from a plurality of elements 302 as introduced above. As shown, the scaffold implant 300 includes an external surface 304, a number of layers 306, a center empty space 308 at a center of the scaffold implant 300, and a representation of one of the elements 302 that form the scaffold implant 300. In some embodiments, the element 302 corresponds to the element 100 of FIG. 1A. FIG. 3A shows the details of the layers 306 and the elements 302 of the scaffold implant 300, while both FIGS. 3A and 3B show the external surface 304 and the center empty space 308 of the scaffold implant 300, FIG. 3B providing a generalized representation of the scaffold implant 300. In some embodiments, the external surface 304 may contact the surrounding native tissue once the scaffold implant 300 is implanted into the patient's body at the implant site. In creating the scaffold implant 300 based on the elements 302, the elements 302 may be joined and/or stacked horizontally and vertically to create the desired 3D shape for the scaffold implant 300.

In some embodiments, as introduced above, the center empty space 308 of the scaffold implant 300 may be completely or partially filled with a medium containing colony-forming units or components (CFUs) comprising a desired cell culture to regenerate or recreate with the scaffold implant 300. Alternatively, or additionally, the empty space may exist in other locations in the scaffold implant 300 and not just at the center of the scaffold implant 300, and these other locations of empty space may be filled with cells. In some instances, certain regions of empty space in the scaffold implant 300 may be filled preferentially. For example, the center empty space 308 at the center of the scaffold implant 300 may be more highly preferred for filling with the CFUs as compared to empty space in between one or more layers of the scaffold implant 300. In addition to the potential center empty space 308 and the empty space that may exist between the layers 306, empty space may exist between the struts of the elements 302, between elements 302, and/or within one or more struts (for example, inside struts that are hollow). In some embodiments, the center empty space 308 may be larger in volume than the empty space between the struts, the elements 302, the layers 306, and/or a combination thereof. In some embodiments, the space between the struts is defined such that it may accommodate injected cells and an injection needle (or similar device) for cell deposition.

In some embodiments, as introduced above, the struts of the elements 302 may comprise macro and/or microscopic elements to improve tissue cell proliferation and the like. For example, in the case of adipose tissue cells, corresponding pores and cavities that receive the injected adipose tissue cells may range from 0.35 mm to 5 mm in size. In some embodiments, the pores and cavities that receive injected adipose tissue cells (or other tissue cell types) may have sizes measured smaller than 0.35 mm or sizes larger than 5 mm. For example, for bone cells, the pores and cavities that receive the bone cells may range from 0.2 mm to 1.2 mm in size, though the pores and cavities may be less than 0.2 mm or larger than 1.2 mm in size. Such dimensions of the pores and cavities may represent the corresponding sizes before any degradation and/or resorption of the scaffold implant 300. As the scaffold implant 300 resorbs/degrades, the empty space between the struts (and other empty space in the scaffold implant 300) may expand over time. In some embodiments (for example, when the empty spaces in the scaffold implant 300 are filled with cells to regenerate, etc.) the scaffold implant 300 itself gradually degrades and/or dissolves (for example, to make room for the regenerating tissue) while the tissue regenerates inside the space previously occupied by the scaffold implant 300 (for example, the struts and nodes). Thus, the tissue cells may fill up the space left behind by the resorption of the scaffold implant 300 (for example, adipose tissue cells when the scaffold implant 300 is used to recreate or regenerate breast tissue). However, the structural properties of the scaffold implant 300 are maintained for a period necessary to keep the excised volume open and provide a framework for the process of regenerating any tissue cells injected into the scaffold implant 300.

In some embodiments, an overall porosity/density of the scaffold implant 300 is the ratio between a volume of the void space (for example, the volume of the pores or cavities) divided by the total volume contained in the scaffold implant 300. For adipose tissue, the porosity of the scaffold implant 300 may range between 80% and 95.5%. For bone tissue, the porosity of the scaffold implant 300 may range between 60% and 95%. In some embodiments, the porosity of the scaffold implant 300, and/or the sizes the pores and cavities, may be determined and/or change based on a concentration of the tissue cells injected into the empty space in the scaffold implant 300.

Example Biomaterials for Manufacturing the Scaffold Implants

As introduced above, the scaffold implants (for example, corresponding to the scaffold implant 300) may be manufactured using implantable materials that are safe for use in humans over long periods of time (for example, periods of time for which implants are expected to remain in patients). In some instances, a number of natural or synthetic materials may be used to manufacture the scaffold implant, individually or in combination. For example, the scaffold implant may be formed from natural materials such as silk fibers, collagen, hyaluronic acid infused materials, and the like. Examples of synthetic, biodegradable polymers or materials for manufacturing the scaffold implant comprise aliphatic polyesters of poly (glycolic acid) (PGA) and poly(lactic acid) (PLA). PGA may have a high crystallinity, a high melting temperature, and a low solubility in organic solvents (in other words, in the patient's body). PLA, on the other hand, may have a much more hydrophobic character than PGA due to the introduction of the methyl group. Thus, PLA has low water uptake and its ester bond is less labile to hydrolysis owing to steric hindrance of the methyl group. Therefore, PLA may degrade more slowly and has higher solubility in organic solvents than even PGA. In some embodiments, copolymers of PLA and PGA (PLGA) can be readily synthesized and used to form the scaffold implant, where the physical properties of the copolymer are regulated by the ratio of glycolic acid to lactic acid in the copolymer. Thus, these copolymers can be used in various applications as biodegradable matrices or scaffold implants in tissue generation and engineering. In some embodiments, such aliphatic polyesters can be readily processed into various physical forms, such as the scaffold implants described herein. Implantation of the scaffold implants formed from the described polymers may lead to host tissue ingrowth throughout the scaffold implant, thereby improving the tissue regeneration associated with the scaffold implants. For example, such polymers are biocompatible and mimic the microenvironment. Thus, the polymers, when used to manufacture the scaffold implant, may provide a correct environment or tissue substrate for the surrounding native tissue to make connections with/invade the scaffold implant structure and connect with the new tissue such as by neovascularization. This may lead to integration of old and new tissue to eventually form one "piece" of tissue, such as an entire breast.

A number of other synthetic polymers can be used to fabricate scaffold implants for tissue reconstruction, regeneration, and the like, such as polycaprolactone, polyanhydrides, poly(amino acids), and poly(ortho esters). Polycaprolactone (PCL) may also be one of the aliphatic polyesters and is a semi crystalline polymer with high solubility in organic solvents and low melting temperature. Thus, the degradation rate of PCL may be slower than that of PGA or PLA, making PCL a good potential option for synthetic polymer scaffold implants. Polyanhydrides may be copolymers of aromatic diacids and aliphatic diacids and may degrade at a controlled degradation rate. The degradation rates of polyanhydrides may be much faster than those of poly (ortho esters) in the absence of any additives, thus making the polyanhydrides less desirable as a copolymer for scaffold implants as compared to other natural and/or synthetic materials. One or more of these biomaterials may be used in a single scaffold implant. In some instances, the selection and composition of the scaffold implant is primarily driven by the tissue to be regenerated, because the tissue to be regenerated may regenerate at different rates, etc., with different scaffold implant materials. For example, when the tissue to regenerate is breast tissue, which comprises more than one type of cell such as adipocytes, fibroblasts, muscle cells, epithelial cells, a particular material, such as PLA or collagen (or a combination thereof), for the scaffold implant may be used as compared to another tissue type.

Stiffness

Figure 4:
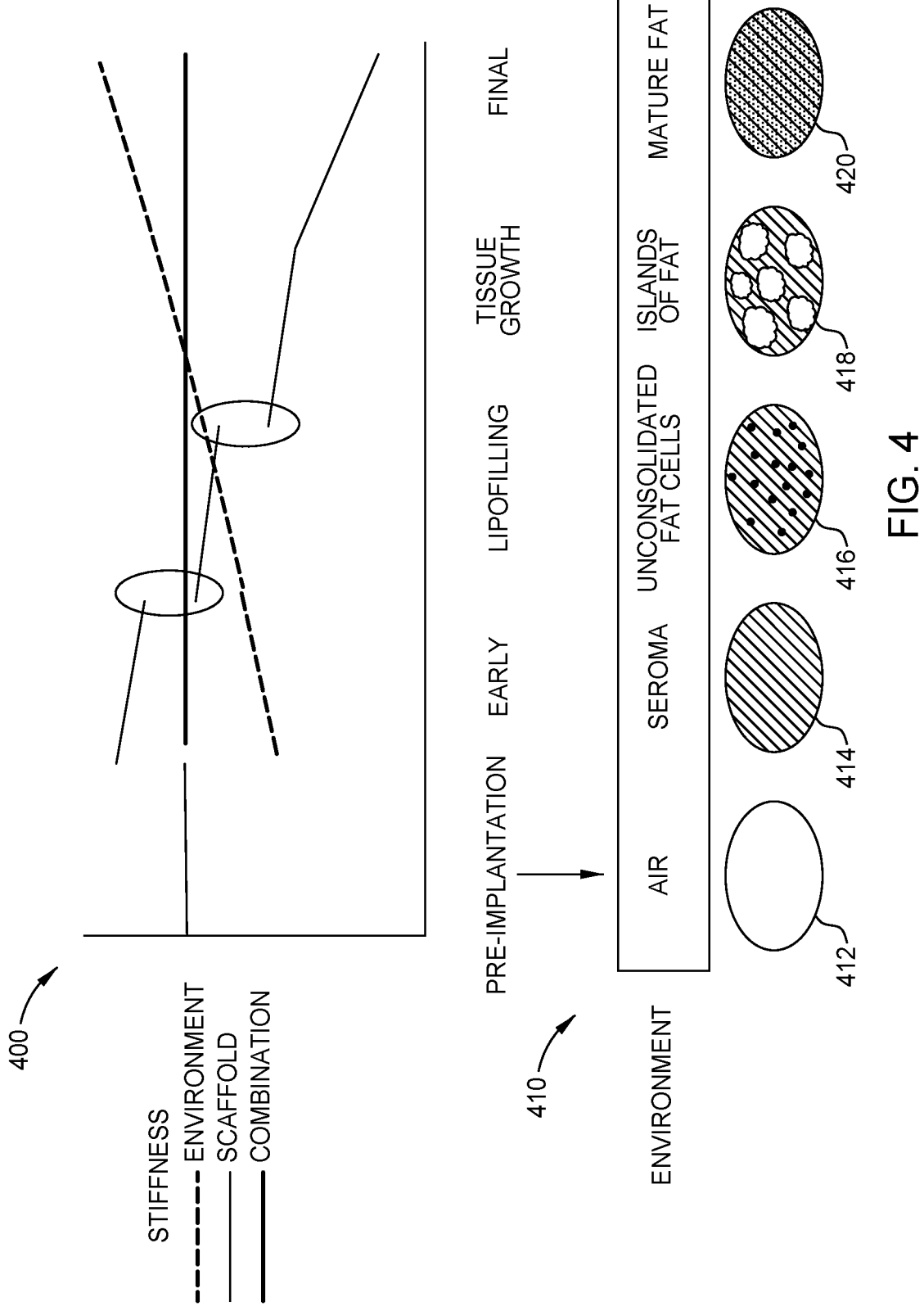
FIG. 4 depicts a stiffness chart showing relationships between the stiffness of various aspects of a tissue regeneration process along a representative timeline of the tissue regeneration process with respect to the environment, in accordance with exemplary embodiments.

FIG. 4 depicts a stiffness chart 400 showing relationships between the stiffness of various aspects of a tissue regeneration process along a representative timeline 410 of the tissue regeneration process with respect to the environment. For example, the stiffness chart 400 showing a progression of stiffness measures (along the y-axis) over time (along the x-axis and in the timeline 410). The stiffness chart 400 shows relative stiffness values for each of: the environment for the tissue regeneration, the scaffold implant for the tissue regeneration, and a combination or total stiffness of the environment and the scaffold implant.

The timeline 410 of the tissue regeneration embodiment includes a progression of the environment during and through a tissue regeneration/creation process. The process starts with air at a preimplantation phase 412, for example, when there is no cell growth. The process then progresses to an early phase 414, when seroma or fluid is building up in the environment, which may be early in the tissue regeneration process. In some embodiments, the process optionally progresses to a lipofilling phase 416, which may be done as a minimally invasive procedure, where unconsolidated fat cells are injected into the environment. Alternatively, the fat cells may continue regenerating as unconsolidated fat cells. The process then progresses to the tissue growth phase 418, during which islands of fat are developing. The process then progresses to the final stage 420, when fat cells have filled a majority or entirety of the environment during final stages of the tissue regeneration process.

As shown in the stiffness chart 400, as the tissue regeneration process progresses, the stiffness values of different components involved in the tissue regeneration process change. For example, at the beginning of the tissue regeneration process (for example, at phase 412), there is no stiffness because this is before implantation of the scaffold implant and tissue cells injection. However, when the tissue regeneration process progresses to the phase 414 in the early phase of the tissue regeneration process, the scaffold implant has its greatest stiffness (and the greatest stiffness in the environment) when recently implanted. During this initial stage, the environment has the least stiffness, making the average of the stiffness values as shown. Through the course of the progression of the tissue regeneration process, the stiffness of the scaffold implant reduces as the scaffold implant begins to degrade. Meanwhile, the environment's stiffness is increasing as the tissue cells grow and strengthen. This trend continues until the scaffold implant is fully degraded (or nearly fully degraded) and the tissue cells have filled (or nearly filled) the environment with the appropriate stiffness.

As shown in the stiffness chart 400, the combination of the stiffness of the environment and the stiffness of the scaffold implant is generally or substantially the same throughout the tissue regeneration process.

Internal Support Structures

In some embodiments, the scaffold implant described herein may incorporate one or more internal structures to help the scaffold implant enable improved tissue cell growth and regeneration. Such internal structures may include injection internal structures and reinforcement internal structures, as described in further detail below with respect to FIGS. 5A and 5B.

Figure 5A:
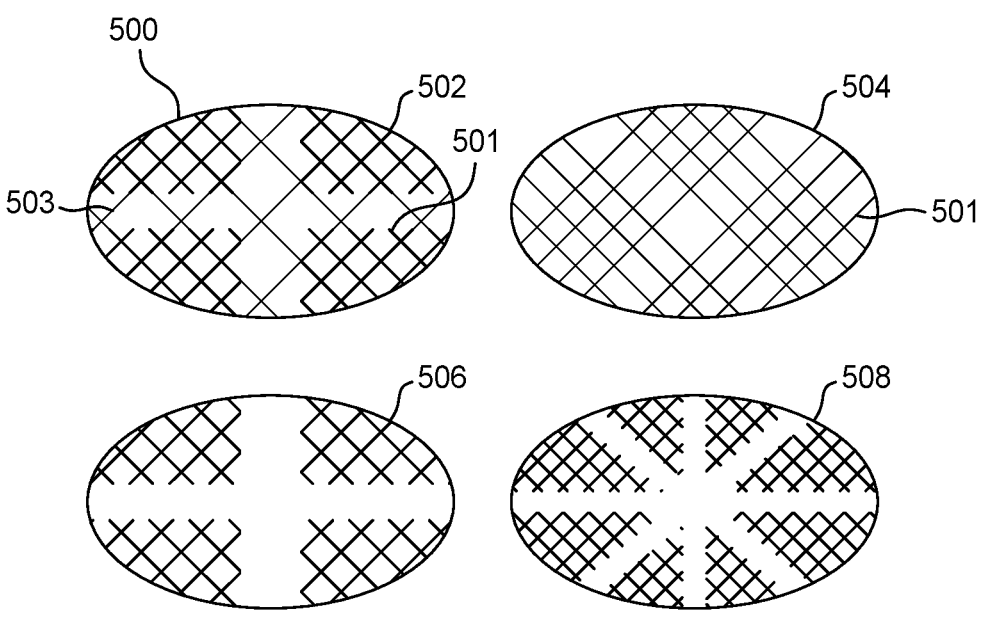
FIGS. 5A and 5B display examples of possible internal structures or reinforcements and their arrangements thereof/ scaffold implant embodiments used with the scaffold implant that can help facilitate injection of the tissue cells into the scaffold implant.

FIG. 5A displays examples of possible injection internal structures/scaffold implant embodiments 502-508 used with the scaffold implant (for example, the scaffold implant 300 introduced above) that can help facilitate injection of the tissue cells into the scaffold implant. Specifically, the injection structures may act as guides for the medical professional to inject cells into the scaffold implant embodiments 502-508. In some embodiments, the scaffold implant may include the embodiments 502-508 to facilitate the injection of tissue cells and/or the homogenous distribution of lipoaspirate or cell culture(s) into the scaffold implant. In certain embodiments, the embodiments 502-508 may have a lower density as compared to remaining portions of the scaffold implant (for example, the struts, etc.). Thus, the embodiments 502-508 may enable filling of the empty spaces in the scaffold implant, thereby acting as preferential filling routes due to the reduced resistance of the embodiments 502-508 as compared to the other, higher density portions of the scaffold implant. These lower density injection internal structures may be surrounded by a protective structure that protects the cells injected or seeded into the scaffold implant, as described further below.

The embodiments 502-508 each show an external structure 500 corresponding to a generic view of the structure of the scaffold implant and injection internal structures 501 that exist inside the structure of the scaffold implant. The first embodiment 502 shows a "cross" type shape formed by two channels that may be filled with lower density internal structures 503 of a as compared to the injection internal structures 501. Thus, the injection internal structures 501 are available for injection of the tissue cells into the scaffold implant. The remaining space in the scaffold implant shows the injection internal structures 501 in a cross-hashed pattern. Using the two channels, a medical professional can inject the tissue cells into the scaffold implant at any location along one or both of the two channels. Thus, the two channels may facilitate injection of the tissue cells into the scaffold implant. The second embodiment 504 shows a central diamond shaped area (empty space) available for injection of the tissue cells into the scaffold implant, surrounded by the injection internal structures 501 (represented by the cross-hashed pattern). Using this central area, a medical professional may inject the tissue cells into the scaffold implant with less resistance than injecting the tissue cells at other locations of the scaffold implant. The third embodiment 506 shows a "cross" type shape formed by two channels (empty space) available for injection of the tissue cells into the scaffold implant. The remaining space in the scaffold implant shows the injection internal structures 501 in a cross-hashed pattern. Using the two channels, a medical professional can inject the tissue cells into the scaffold implant at any location along one or both of the two channels. Thus, the two channels may facilitate injection of the tissue cells into the scaffold implant. The fourth embodiment 508 shows a "star" type shape formed by four (or more) channels (empty space) available for injection of the tissue cells into the scaffold implant. The remaining space in the scaffold implant shows the injection internal structures 501 in the cross-hashed pattern. Using the various channels, the medical professional can inject the tissue cells into the scaffold implant at any location along one or more of the channels to facilitate injection of the tissue cells into the scaffold implant.

Figure 5B:
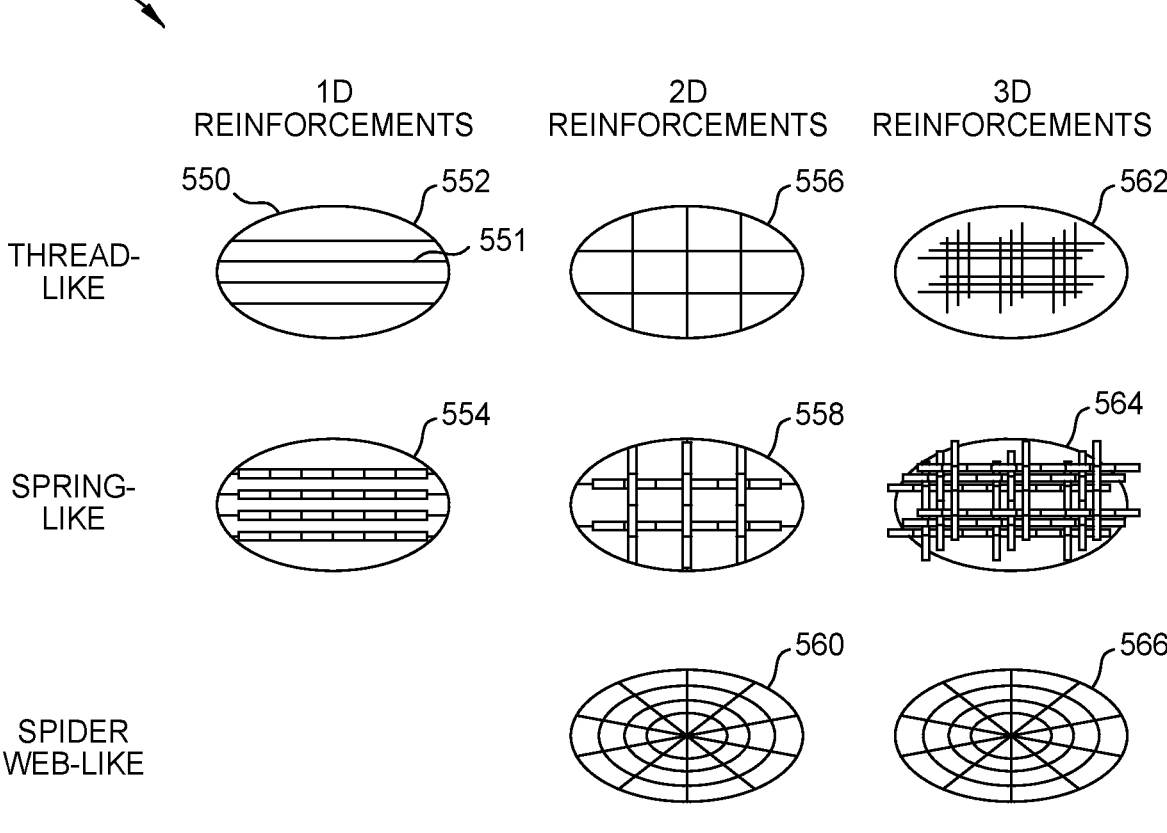

FIG. 5B displays examples of the reinforcement injection internal structures/scaffold implant embodiments 552-566 as used with the scaffold implant (for example, the scaffold implant 300 introduced above) to help protect tissue cells injected into the scaffold implant. In some embodiments, the scaffold implant may include the embodiments 552-566 to improve protection and support for the injected tissue cells in the scaffold implant. In certain embodiments, the scaffold implant may further comprise the reinforcement internal structures that serve as reinforcements to the scaffold implant and restrict excessive stresses and strains to the newly developing tissue. Thus, these internal structures may also facilitate the proliferation of the tissue cells and the growth of the tissue along a surface of the internal structures. In certain embodiments, the reinforcement internal structures may have a higher density as compared to the rest of the scaffold implant. For example, the reinforcement internal structures may comprise one or more struts, one or more layers, one or more grid like structures, and/or one or more concentric layers, such as portions of spheres or spheroids.

The embodiments 552-566 each show an external structure 550 corresponding to a generic view of the structure of the scaffold implant and reinforcement internal structures 551 that exist inside the structure of the scaffold implant. These reinforcement internal structures may be formed from a different material than the structure of the scaffold implant to obtain the increased or higher density. In certain embodiments, the reinforcement internal structures may be hollow, thereby preventing the space contained between them from collapsing and preventing damage to the cells contained. In some embodiments, the reinforcement internal structures may be of any shape. In some embodiments, the reinforcement internal structures may comprise one-, two- or three-dimensional structures, as shown in FIG. 5B. The 1D reinforcement internal structures may comprise threadlike 552 or spring like 554 structures that exist along a single dimension or axis (for example, provide reinforcements substantially in a single direction of a plane). The 2D reinforcement internal structures may comprise threadlike 556, spring like 558, and/or spider web like 560 structures that exist along two dimensions or axes (for example, provide reinforcements substantially in all directions of a plane). The 3D reinforcement internal structures may comprise threadlike 562, spring like 564, and/or spider web like 566 structures that exist along three dimensions or axes (for example, provide reinforcements substantially in all directions of and orthogonal to a plane).

In some embodiments, the scaffold implant may further comprise environment or surrounding tissue interfacing elements that provide added stability to the scaffold implant and anchor the scaffold implant to the native tissue surrounding a site where the scaffold implant is implanted. These interfacing elements may help the scaffold implant avoid experiencing shear or other movement relative to the surrounding native tissue that could cause damage to or restrict neovascularization. In certain embodiments, the interfacing elements may comprise one or more of protrusions (such as spikes), bumps, prominences, protuberances, overhangs, excrescences, and/or combinations thereof, any of which can provide additional anchoring between the scaffold implant and the surrounding tissue. In some embodiments, the interfacing elements may be fixedly and/or detachably attached to one or both of the surrounding tissue and the scaffold implant. The interfacing elements may be deployable, such that the interfacing elements can be deployed once or while the scaffold implant is implanted into the patient. For example, the medical professional performing the procedure to implant the scaffold implant may deploy the interfacing elements and cause the interfacing elements to protrude in the surrounding tissue upon command. The medical professional may use a mechanism to deploy the interfacing elements to cause the interfacing elements to remain protruded, thereby ensuring that the scaffold implant is secured into the surrounding tissue. In some embodiments, the mechanism comprises intraoperatively applying pressure on an inner end of the additional interfacing elements (that protrude from the scaffold implant), resulting in an outward movement of the additional interfacing elements into the surrounding native tissue. The deployed interfacing elements may be locked in their deployed state by a locking means (for example, such as one or more markings, indentations, and/or threads such as screw threads of varying length depending on the depth of anchoring needed). In some embodiments, the additional interfacing elements of the scaffold unit are rounded to limit stress, wounding, and/or scarring of the surrounding tissue when the additional interfacing elements are in contact with the surrounding tissue.

An overall interfacing surface of the scaffold implant may comprise all exterior surfaces of the scaffold implant that contact the surrounding native tissue. The interfacing surface may be designed to promote an exchange of nutrients with the surrounding tissue, thereby enabling the scaffold implant to provide nutrients to the tissue cells injected into the scaffold implant. In some embodiments, a density of the scaffold implant structure is reduced at the interfacing surface to allow interconnections with the surrounding tissue while keeping stress to a minimum. For example, portions of the scaffold implant that protrude (for example, portions that interconnect with the surrounding tissue) from the scaffold implant may have a reduced density as compared to portions of the scaffold implant that protrude less (or do not protrude) from the scaffold implant or that do not come in direct contact with the surrounding tissue (such as inner layers of the scaffold implant). This reduced density may provide for better attachment, grounding, and/or support of the scaffold implant with the surrounding tissue.

In certain embodiments, the scaffold implant comprises additional features to facilitate the spatial identification of the scaffold implant during diagnostic and other procedures. The spatial identification aims to support the successful planning and administration of radiotherapy or the quantification of the progression in scaffold implant resorption (if any). Furthermore, the spatial identification may enable improved identification for the injection of the lipoaspirate into the scaffold implant, thereby avoiding additional surgical procedures.

Procedure for Implanting the Scaffold Implant

The scaffold implant described herein is intended to be surgically implanted in a region of the patient's body (for example, a reconstruction area or region) to replace a volume of tissue that did not or no longer exists.

Before the scaffold implant is implanted into the patient and even during early stages of the tissue generation process, the scaffold implant includes one or more empty spaces. The one or more empty spaces may comprise the empty center, corresponding to the center empty space 308, and/or the empty spaces that exist between the struts, layers, and/or the like of the scaffold implant. These empty spaces of the scaffold implant may be filled by injection, infusion, or grafting of tissue cells (for example, stem cells or fat tissue), which are preferably autologous, soon after the medical professional successfully implants the scaffold implant. Any lipofilling process associated with the scaffold implant may be delayed for a period of time, which may range from several days to several months based on how well the scaffold implant adheres to the native surrounding tissue. During this period of delay, the patient may or may not undergo radiation therapy. This delayed period also has beneficial effects. For example, during this delay period, neovascularization of the implant, which may be necessary to supply oxygen to newly filled tissue cells. The neovascularization may also enable formation of the natural extracellular matrix that provides a structural framework for the transplanted cells and formation of connective tissue (for example, within the scaffold implant and/or between the scaffold implant and the surrounding native tissue). Thus, the neovascularization may help support the new tissue and provide/exchange nutrients with/to the new tissue.

During the lipofilling process, the medical professional may insert a needle (or corresponding device) into the empty spaces of the scaffold implant and inject the liposuction material. As introduced above, the empty spaces between the struts and the empty center of the scaffold implant are designed such that the scaffold implant easily accommodates the injection needle. Thus, using the scaffold implant described herein, such lipofilling processes can be performed during a minimally invasive surgery (MIS) to deposit the tissue cells.

The scaffold implant may also be used for in-vitro tissue regeneration. For example, a particular scaffold implant is patient specific and is loaded with adequate CFU comprising of desired cells for that patient, such as adipose stem cells. An external bioreactor may then store the scaffold implant such that the external bioreactor mimics the native tissue environment such that the storage of the scaffold implant in the external bioreactor promotes tissue regeneration in the scaffold implant. Once a desired cell/tissue volume is achieved or after a threshold period of time, the medical professional implants the scaffold implant, along with the new cells/tissue growth generated during the storage in the external bioreactor, into the patient in a single surgical procedure. Thus, the storage of the scaffold implant with loaded tissue cells may eliminate additional injection procedures, improve implant acceptance, and promote successful implant procedures. In certain embodiments, different types or different scaffold implants can be used with different types of tissue. Thus, the scaffold implant may dissolve in the bioreactor and, during an implant surgery, the surgeon may insert a partly or fully developed tissue into the patient without the need for the scaffold implant. Thus, the scaffold implant may be used to generate the implant tissue without being implanted into the patient.

In some embodiments, the scaffold implant may serve as a surrogate to generate tissue for implanting with another scaffold implant or without a scaffold implant into a patient. In some instances, the scaffold implant may act as an in-vivo bioreactor, wherein the scaffold implant is implanted at a donor site from where the tissue cells will later be harvested for an implant procedure. Such a donor site (and thus, such a site where the scaffold implant acts as the in-vivo bioreactor) may include the abdomen (or a site with abundant fat). Alternatively, or additionally, the scaffold implant may be pre-loaded with growth factors or ASCs to promote the tissue regeneration and vascularization on the scaffold implant. In some embodiments, once the desired amount of tissue has been regenerated using the in-vivo bioreactor scaffold implant, the medical professional removes the in-vivo bioreactor scaffold implant from the donor site (along with the pre-grown and vascularized tissue). The medical professional then transplants the scaffold implant with the pre-grown and vascularized tissue or just the vascularized tissue in the breast region instead of having to resect part of the donor tissue.

In some embodiments, the scaffold implant may be surface treated with growth factors, such as vascular endothelial growth factor (VEGF), fibroblast growth factor-2 (FGF-2), epidermal growth factor (EGF), fibronectin and other substrates that promote tissue regeneration in and/or on the scaffold implant.

Figure 6:
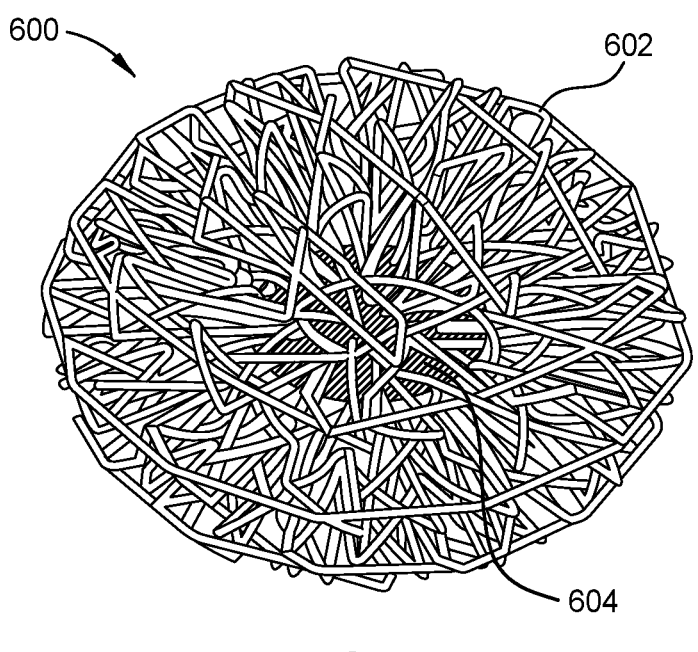
FIG. 6 depicts a perspective view of an embodiment of a scaffold implant, in accordance with exemplary embodiments.

FIG. 6 depicts a perspective view of an embodiment of a scaffold implant 600, in accordance with exemplary embodiments. More specifically, the scaffold implant 600 may include at least two patterns of elements, shown as elements or patterns 602 and 604 wherein 604 may be used to fill/reduce/modify the central empty space. The different patterns of elements 602 and 604 may enable the scaffold implant 600 to have improved flexibility as compared to single element scaffold implants.

Figures 7A, 7B, 7C, 7D:
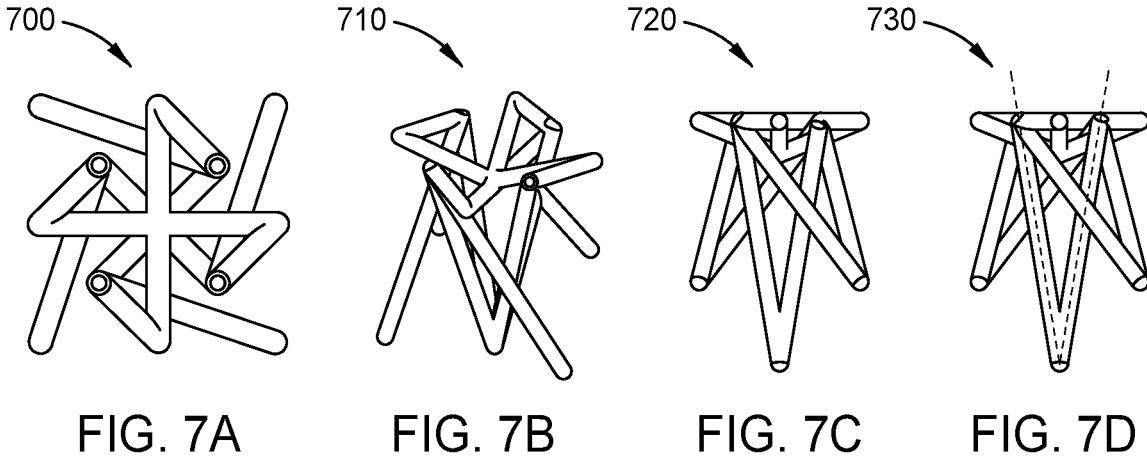
FIGS. 7A-7D depict variations of elements that can be arranged to form a partial arrangement of one or more layers of a scaffold implant, in accordance with exemplary embodiments.
Figure 7E:
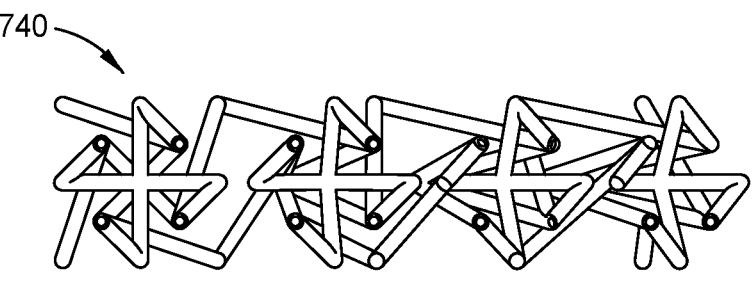
FIG. 7E depicts how neighboring elements may be interconnected in one or more layers, in accordance with exemplary embodiments.

FIGS. 7A-7E depict variations of the elements 700-730 that can be arranged to form a partial arrangement 740 of one or more layers of the scaffold implant, in accordance with exemplary embodiments. The elements 700-730 show variations of numbers of struts, nodes, thickness or hollowness of the struts, and shape/configuration of the elements 700-730, where the element 730 includes hollow struts. FIG. 7E shows how neighboring elements may be interconnected in one or more layers via horizontal stacking of elements to form the partial arrangement 740. In some instances, the neighboring elements can be stacked or layered vertically and/or horizontally, or any combination thereof.

Layered Scaffold Implant Structures

As introduced above, the scaffold implants described herein may comprise multiple layers. In some embodiments, each of the multiple layers are formed by an arrangement of elements, such as the elements 100. Further details of such layered scaffold implants are provided below with respect to FIG. 8.

Figure 8:
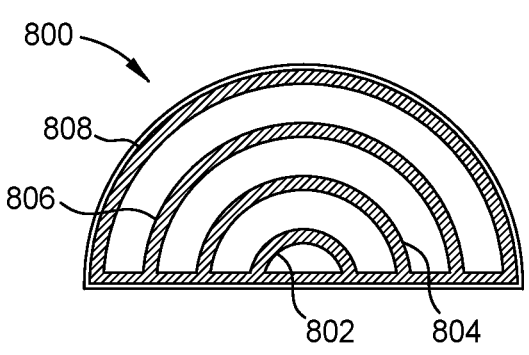
FIG. 8 depicts an example of a scaffold implant (or a portion thereof) comprising a number of structural layers.

FIG. 8 depicts an example of a scaffold implant 800 (or a portion thereof) comprising a number of structural layers 802-808. The scaffold implant 800, which may correspond to the scaffold implant 300, shows the structural layers 802-808 as a series of concentric arcs. In some embodiments, one or more of the layers 802-808 comprise a hybrid structure made up of the macro and/or microscopic elements introduced above. In certain embodiments, the microscopic elements may correspond to the pores and/or cavities, wherein the pore/cavity size and, thus, density of the microscopic elements for different layers 802-808 is proportional or otherwise related to the different stages of a cell growth cycle.

For example, the growth of the tissue cells in the scaffold implant 800 may not be uniform across all of the layers 802-808. For example, in some instances, the tissue cell growth along the outermost layer 808 may occur more quickly than tissue cell growth along the innermost layer 802, or vice versa. Thus, the different layers 802-808 may have microscopic elements (such as pore/cavity size and density) for different element variations or configurations to accommodate such different growth rate expectations. As such, the variations or combinations of the microscopic elements may promote, for example, adipocytes regeneration, proliferation, and attachment at different rates for the different layers 802-808.

As introduced above, an overall structure or shape of the scaffold implant may depend on the shape of the missing volume of tissue to be regenerated. As such, the arrangement (and, thus, the shape) of the layers 802-808 of the scaffold implant may also be dependent on the shape of the missing volume of tissue being filled. For example, where the space to be filled is spherical, each layer 802-808 may correspond to concentric spheres with different radii. Thus, each layer 802-808 may be one inside the other, with the outermost layer 808 having the smallest pore size and the innermost layer having the largest pore size. As introduced above, this may mimic the different stages of cell differentiation and growth, which in the case of adipocytes, has been observed to progress from the outermost layer 808 of the scaffold implant to the innermost layer 802. This may also ensure or promote uniform cell distribution.

As further described above, the scaffold implant may be made from one or more bioresorbable materials. To adapt that feature with the multilayered scaffold implant 800, each layer 802-808 may be formed from different bioresorbable materials or otherwise resorb at different rates within the patient's body. For example, it may be desirable for the outermost layer 808 to resorb when the tissue cells grown in the empty space nearest the outermost layer 808 have achieved a desired confluency and/or have started making vascular connections (within the tissue cells and/or with the surrounding native tissue). It may be desirable for the second outermost layer 806 to dissolve next and so on, such that cellular proliferation is aligned with different stages of the cell growth cycle. Thus, the innermost layer 802 of the scaffold implant 800 may contain the largest pores so that it can provide adequate attachment to mature adipocytes or to the transplanted fat tissue with lipid droplets in the middle and also be formed by the material that is resorbed slower than any of the other layers 804-808. This attachment may enhance cell-cell interaction and prevent loss of fat tissue over time, making sure that the missing tissue remains filled even when the scaffold unit is resorbed. Thus, the different layers 802-808 of the scaffold implant 800 may have various parameters that enable each layer to provide benefits to the tissue cell growth cycle particular to that layer's location in the scaffold implant 800.

Further, subsequent layers 802-808 may be coated with one or more growth factors, where the growth factors may be different for different layers to promote the best cell growth cycle for the entire scaffold implant. Similarly, different layers 802-808 may promote different growth and differentiation of cells based on different volumes of CFUs being deposited on the layer based on the layer's differentiation cycle and timing in the cell growth cycle.

In some embodiments, the multiple layers 802-808 of the scaffold implant 800 may be fixedly and/or detachably attached to each other and/or the surrounding native tissue using one or more of bioresorbable, functional interfacing elements. Examples of such interfacing elements include fibrin glue and the like and structural elements, such as microscopic and/or macroscopic bioresorbable hooks, spines, cilia-like structures, sutures, knots, and the like.

In certain embodiments, the outermost layer 808 of the scaffold implant 800 may have an interfacing element comprising an additional lining formed from a spongy or liquid filled (or similar) material, such as shown by the added thickness of the outermost layer 808 in FIG. 8. This additional lining may absorb mechanical shocks to the scaffold implant 800 and may help keep the inner layers 802-806 of the scaffold implant 800 intact, while allowing some movement, and thereby maintaining flexibility, of the scaffold implant 800. In certain embodiments, the outermost layer 808 may be customized to allow a one-way transfer of nutrients into the scaffold implant 800 and permit gaseous diffusion between the scaffold implant 800 and the surrounding native tissue so that the new tissue cells do not undergo hypoxia and/or have adequate oxygen for growth. In certain embodiments, the outermost layer 808 may be hydrophilic or treated with an appropriate chemical that permits entry into the scaffold implant 800 of specific certain molecules. In certain embodiments, the scaffold implant 800 comprises hollow tubular connecting elements to enhance further vascularization, where the hollow tubular connecting elements provide a path from the empty spaces where cells are expected to grow to the surrounding native tissue.

Controlled Release of Compressed Layers

In certain embodiments, the plurality of layers that form the scaffold implant may be released individually/consecutively, as the different portions of the scaffold implant resorbs. In some embodiments, this type of timed or consecutive release may lead to a change in the shape and/or mechanical properties of the scaffold implant over time. For example, the timed release may change the flexibility of the scaffold implant or increase a maximal expansion of the scaffold implant. For example, with respect to the change of the flexibility of the scaffold implant, the different layers may have different flexibility properties depending on, in some instances, their timed release. Thus, when the outermost layer is resorbed, the next outermost layer (which does not have the additional lining that the outermost layer had and may comprise a different material) may present different flexibility parameters than the outermost layer.

Figure 9A:
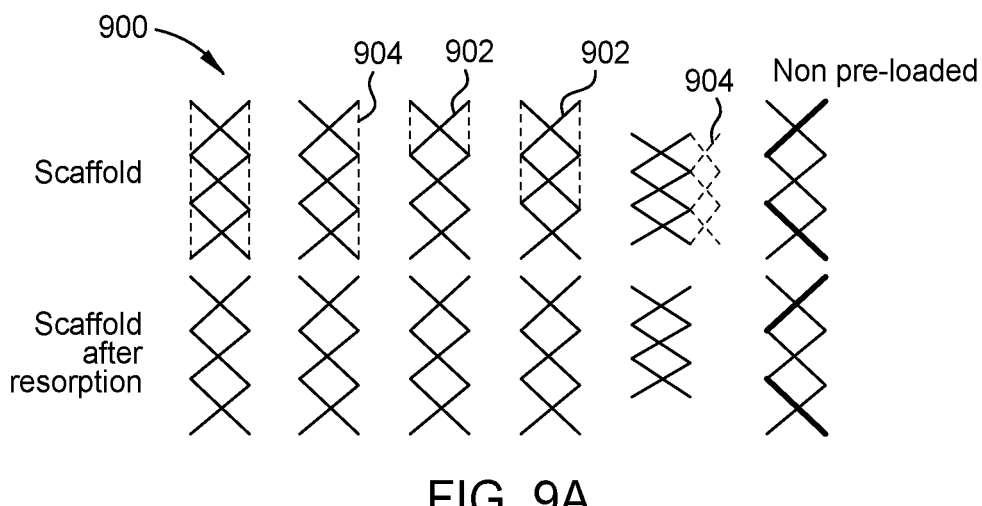
FIGS. 9A and 9B illustrate how flexibility can be achieved for the scaffold implant comprising a plurality of layers, in accordance with exemplary embodiments.

FIG. 9A illustrates multiple, simplified views (rows) of a scaffold implant 900 comprising a plurality of layers 902 and release mechanisms 904 that apply force to the layers 902 of the scaffold implant 900. The scaffold implant 900 and the plurality of layers 902 in FIG. 9A are not preloaded and are not compressed. The release mechanisms 904 instead manage a flexibility of the scaffold implant 900 and enable the gradual release of individual layers 902 of the plurality of layers 902 to gain flexibility. Row 1 represents the scaffold implant 900 before resorption of the release mechanisms 904. Row 2 represents the scaffold implant 900 after resorption of the release mechanisms 904. For the scaffold implant 900, the release mechanisms 904 may function to reduce flexibility of the scaffold implant 900 until the release mechanisms 904 resorb. Thus, the scaffold implant 900 of the row 2 may have increased flexibility as compared to the scaffold implant 900 of the row 1. In some embodiments, the release mechanism 904 may be controlled manually, for example, by using a suction driven force mechanism to release the layers 902 one or more at a time, as shown in FIG. 9A. In some embodiments, the release mechanisms 904 may "activate" as a function of time, where the release mechanisms 904 are bioresorbable and resorb over a period, after which the layers 902 are released one or more at a time.

Figure 9B:
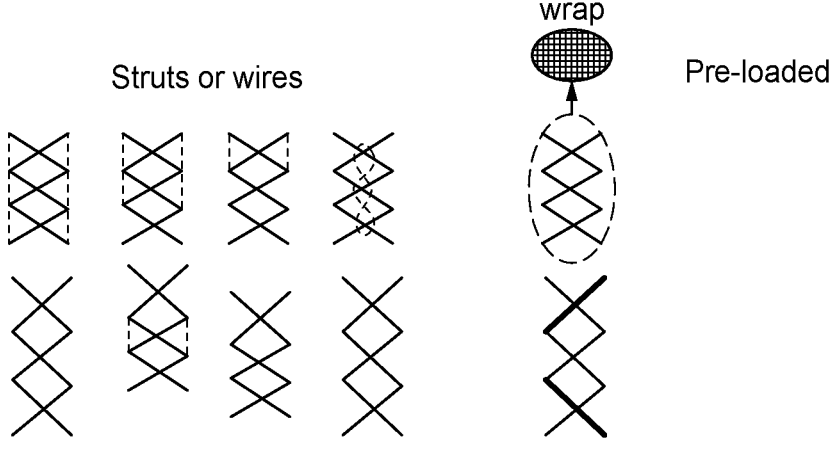

FIG. 9B illustrates multiple, simplified views (rows) of the scaffold implant 900 comprised of the plurality of layers 902 and release mechanisms 904 that apply tension to and compress the layers 902 of the scaffold implant 900. The scaffold implant 900 and the plurality of layers 902 in FIG. 9B are preloaded. Similar to FIG. 9A, the release mechanisms 904 enable the gradual release of individual layers 902 of the plurality of layers 902, thereby releasing corresponding tension. Row 1 represents the scaffold implant 900 before resorption of the release mechanisms 904, when one or more of the layers 902 is compressed by one or more of the release mechanisms 904. Row 2 represents the scaffold implant 900 after or during (see column 2, row 2, wherein the top X is released vs the subsequent X which is still in tensioned state) resorption of the release mechanisms 904 and release of the corresponding tension. For the scaffold implant 900, the release mechanisms 904 may function to reduce size and flexibility of the scaffold implant 900 until the release mechanisms 904 resorbs. Thus, the scaffold implant 900 of the row 2 may have increased flexibility and increased size as compared to the scaffold implant 900 of the row 1. In some embodiments, the release mechanism 904 may be controlled manually, for example, by using a suction driven force mechanism to release the layers 902 one or more at a time, as shown in FIG. 9B. In some embodiments, the release mechanisms 904 may "activate" as a function of time, where the release mechanisms 904 themselves are bioresorbable and resorb over a period, after which the layers 902 are released one or more at a time as the corresponding release mechanisms 904 release.

Alternatively, or additionally, the scaffold implant is pre-tensioned before implantation and aspects thereof are kept in this pre-tensioned state using one or more physical connectors, such as clips, springs, and the like. The physical connectors can then be released to enable one or more of the plurality of layers 902 to be released. As such, when the physical connectors are removed or released, the pre-tensioning of the scaffold implant 900 (and, thus, the plurality of layers 902 of the scaffold implant 900) may cause the pre-tensioned layer 902 or layers 902 to be released and acquire an un-tensioned form. The physical connectors may be internal (for example, wires, struts, or the like) or external (for example, a wrap, and the like). After resorption or removal of the physical constraints, the force of the pretension will be removed, and the scaffold implant 900 and the layers 902 will operate with their respective mechanical or physical properties.

Figure 10A:
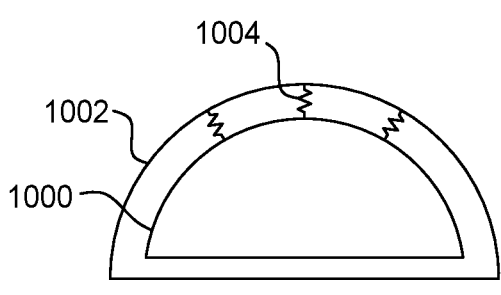
FIG. 10A illustrates how a scaffold implant may be encased or enclosed in a domed shell with internal structures separating the scaffold implant from the domed shell, in accordance with exemplary embodiments.

FIG. 10A illustrates how a scaffold implant 1000 may be encased or enclosed in a domed shell 1002 with internal support structures 1004 or similar structures separating the scaffold implant 1000 from the domed shell 1002. In some embodiments, the scaffold implant 1000 corresponds to one or more of the scaffold implant 300, 800, and/or 900. In some embodiments, in addition to the domed shell 1002, the scaffold implant 1000 may also comprise an inner domed portion (or concentric arcs, similar to the structure described with reference to FIG. 8) that is also connected to the scaffold implant 1000 using one or more bioresorbable connecting elements (not shown).

In some embodiments, the internal support structures 1004 exert a force on the scaffold implant 1000, which causes the scaffold implant 1000 to be internally loaded or pre-tensioned. When the internal support structures 1004 are removed (or, when formed from bioresorbable materials, resorbed) the tension from the internal support structures 1004 is removed and the scaffold implant expands or becomes uncompressed. In certain embodiments, the tension on the scaffold implant 1000 promotes cell growth where, as the scaffold implant 1000 is resorbed, the space occupied by the scaffold implant 1000 is filled with regenerating tissue cells. In some embodiments, different layers of the scaffold implant 1000 resorb at different rates such that inner layers are resorbed more slowly or after outer layers of the scaffold implant 1000.

Figure 10B:
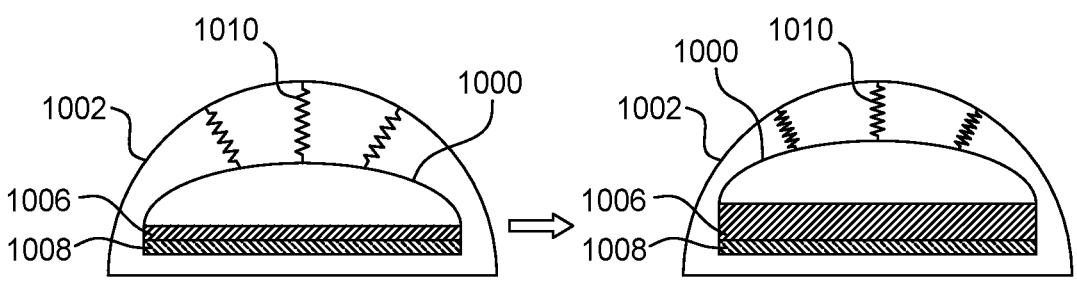
FIG. 10B illustrates how the scaffold implant of FIG. 10A may further comprise a number of layers (for example, compartments or shells) within the scaffold implant, in accordance with exemplary embodiments.

FIG. 10B illustrates how the scaffold implant 1000 of FIG. 10A may further comprise a number of layers 1006 and 1008 (for example, compartments or shells) within the scaffold implant 1000. In some embodiment, each layer 1006 and 1008 may comprise a layered component or piece of the scaffold implant 1000. Furthermore, the layers 1006 and 1008 may be in proximity and/or connected with each other, where the layers 1006 and 1008 either touch or are within a threshold distance of each other. In some embodiments, the layers 1006 and 1008 are in proximity with each other where the layers 1006 and 1008 are next to, above/below each other, within a threshold distance of each other, close to each other, or the like. For example, the layers 1006 and 1008 are in proximity with each other when one layer covers the other layer (for example, overlaps the other layer) or neighbors the other layer. The scaffold implant 1000 may comprise internal support structures 1010 that impart a force on the layers 1006-1008 and keep them compressed and/or in proximity with each other. In some embodiments, the layers 1006 and 1008 may have shapes that are the same or substantially the same. For example, when the layers 1006 and 1008 are stacked on top of each other, the layer 1006 may have a slightly different shape than the layer 1008 (for example, slightly larger, smaller, contoured slightly differently, and so forth) while maintaining substantially the same shape. For example, in some aspects, the shape of a first layer 1006 (or layered structure) conforms to a shape of a second layer 1006 (or layered structure) in that it follows a similar contour.

In certain embodiments, the plurality of compartments (corresponding to the layers of the scaffold implant 1000, such as layers 802-808) may be compressed together such that cell growth occurs on the topmost layer. The cell growth may also be controlled by seeding the layers 1006 and 1008 with cells layer by layer in multiple sessions or chemically activating cell growth on different layers (for example, the layers 1006 and 1008) at different time intervals. Thus, the cell growth cycle can utilize the different layers 1006 and 1008 at different times as appropriate for the particular stage of the cell growth cycle.

In some embodiments, the internal support structures 1010 comprise multiple levels or layers of support structures such that some internal support structures 1010 apply force to keep the layer 1006 compressed and some other internal support structures 1010 apply force to keep the layer 1008 compressed. These different sets of internal support structures 1010 may resorb at different rates based on when the layer 1006 and the layer 1008 are to be expanded relative to the cell growth cycle. In some embodiments, the release of subsequent compartment may be controlled by varying the thickness of the springs. In some embodiments, instead of internal support structures 1010 connected to the domed shell 1002 to delay release of the layers 1006 and 1008, the layers 1006 and 1008 themselves may include one or more components between each other that enable release of subsequent compartments relative to an expected resorption rate of the components in vivo. FIG. 10B may further show how the layer 1006 may expand in size while the layer 1008 remains relatively compressed.

Figure 10C:
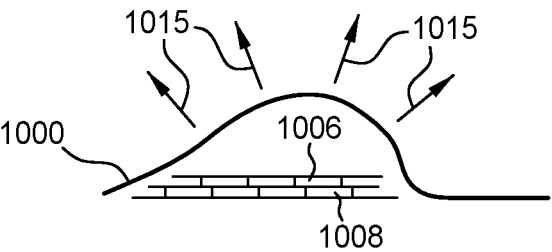
FIG. 10C illustrates how the scaffold implant having two layers may have suction or similar force applied thereto, in accordance with exemplary embodiments.

In some embodiments, suction 1015 may be applied to the outermost layer 1006 of the scaffold implant 1000 to cause the outermost layer 1006 to expand and expose itself to the cell growth. For example, as shown in FIG. 10C, the suction may also be used to help manipulate a desired shape of the scaffold implant 1000 and/or the layers 1006 and 1008 therein. FIG. 10C shows the scaffold implant 1000 having two layers 1006 and 1008 therein, with suction being applied to an outer surface of the scaffold implant 1000. In some embodiments, the suction can later be applied to the layer 1006 to expand the layer 1006, in accordance with the cell growth cycle, followed by to the layer 1008. As such, the different layers 1006 and 1008 of the scaffold implant can be expanded at the appropriate times to encourage and maintain tissue cell growth in and on the scaffold implant 1000.

Use of Pre-Tensioned Scaffold Implant for Bone Applications

As introduced above, the scaffold implant may be used in bone applications, where a section or portion of bone is being repaired or replaced.

Figure 11:
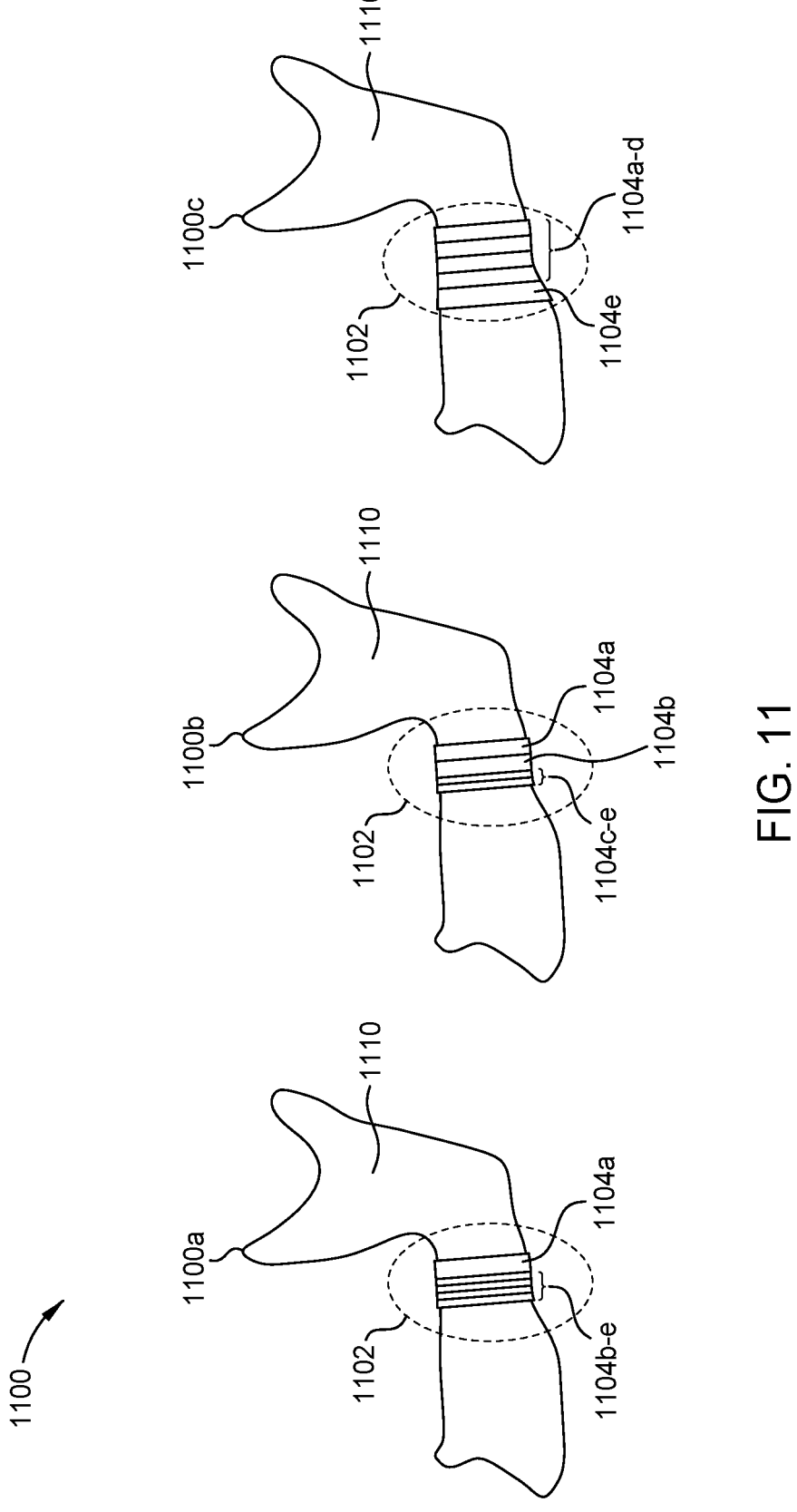
FIG. 11 depicts an embodiment of performing bone distraction on a section of bone using the principle of timed removal of tension on a tensioned scaffold implant according to a cell growth cycle, in accordance with exemplary embodiments.

FIG. 11 depicts an embodiment 1100 of performing bone distraction on a section of bone 1110 using the principle of timed removal of tension on a tensioned scaffold implant 1102 according to a cell growth cycle. The embodiment 1100 depicts how the bone distraction with the scaffold implant 1102 may be used as an alternative to current distractor devices. The current distractor devices have many disadvantages such as social inconvenience, bulkiness, facial scars, and a subsequent surgical procedure for removal of the distractor devices.

As shown, the scaffold implant 1102 comprises a plurality of layers 1104a-1104e in different states or conditions. The embodiment 1100 comprises three stages 1100a, 1100b, and 1100c that occur with the passage of time after the scaffold implant is implanted in the patient.

During the stage 1100a, the scaffold implant 1102 includes a single layer 1104a in a first state of having no tension (any pretension has been released) but the bone tissue regeneration has not yet commenced. For example, the seed cells may not yet have been injected or the seed cells may not yet been activated. Also, during the stage 1100a, the remaining layers 1104b-1104e are in a tensioned stage.

During the stage 1100b, the scaffold implant 1102 includes two layers that are not tensioned. Specifically, the layer 1104a is not tensioned and is in bone tissue regeneration while the layer 1104b is not tensioned but not yet performing the bone tissue regeneration of the cell growth cycle. The remaining layers 1104c-1104e are in a tensioned stage.

During the stage 1100c, the scaffold implant 1102 includes all layers in the untensioned/relaxed/unloaded state. Specifically, the layers 1104a-1104d are not tensioned and performing the bone tissue regeneration while the layer 1104e is not yet performing the bone tissue regeneration.

The consecutive release of each layer 1104 of the scaffold implant 1102 may be aligned to the speed of bone regeneration within each layer and the corresponding cell growth cycle. Thus, the scaffold implant 1102 can replace the currently used distractor device. Examples of bone distraction use cases may relate to the mandible, cranial vault, tibia, femur, humerus or other applications where distractor devices are generally employed.

Use of Pre-Tensioned Scaffold Implant for Breast Reconstruction

Figure 12:
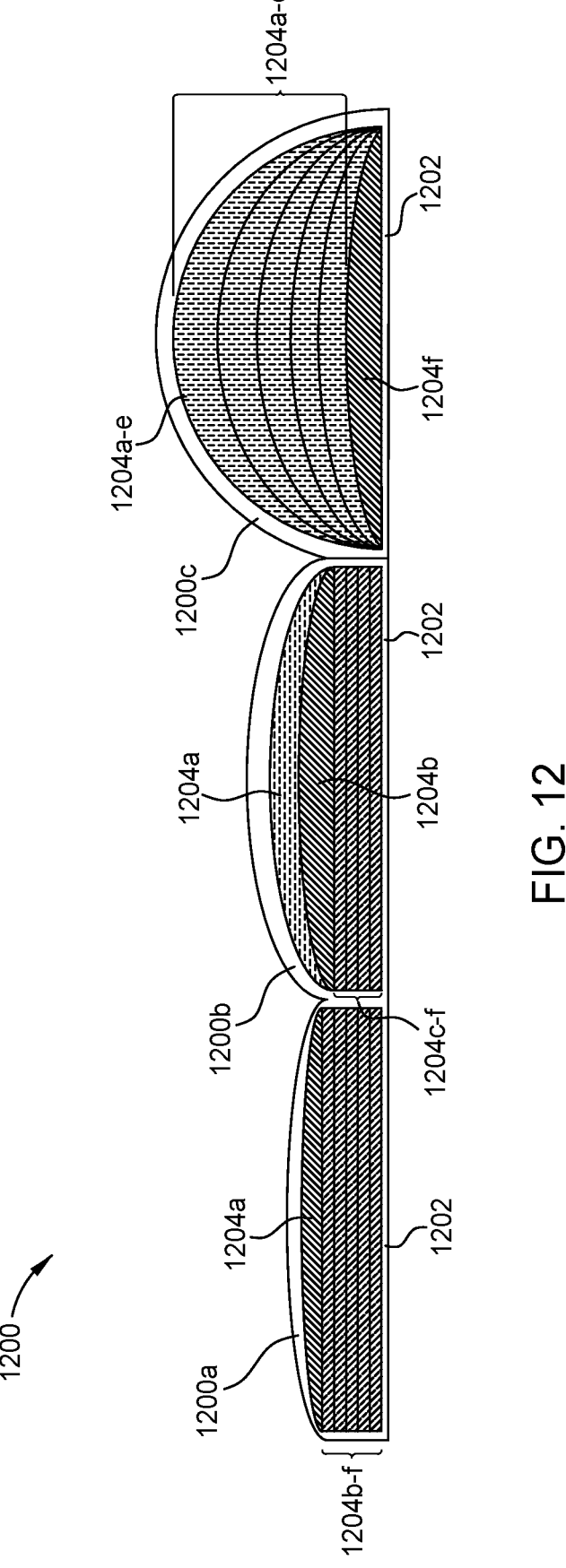
FIG. 12 depicts an embodiment of performing tissue regeneration for breast tissue using the principle of timed removal of tension on a tensioned scaffold implant according to a cell growth cycle, in accordance with exemplary embodiments.

FIG. 12 depicts an embodiment 1200 of performing tissue regeneration for breast tissue using the principle of timed removal of tension on a tensioned scaffold implant 1202 according to a cell growth cycle. The embodiment 1200 may be similar to the embodiment 1100 but as applied to breast tissue instead of bone tissue. The embodiment 1200 depicts how to regenerate breast tissue with the scaffold implant 1202. The scaffold implant 1202 may comprise features of the scaffold implant 300, 800, and/or 900.

As shown, the scaffold implant 1202 comprises a plurality of layers 1204a-1204f in different states or conditions. The embodiment 1200 comprises three stages 1200a, 1200b, and 1200c that occur with the passage of time after the scaffold implant 1202 is implanted in the patient.

During the stage 1200a, the scaffold implant 1202 includes a single layer 1204a in a first state of having no tension (any pretension has been released) but the breast tissue regeneration has not yet commenced. For example, the seed cells may not yet have been injected or the seed cells have not yet been activated. Also during the stage 1200a, the remaining layers 1204b-1204f are in a tensioned stage.

During the stage 1200b, the scaffold implant 1202 includes two layers that are not tensioned. Specifically, the layer 1204a is not tensioned and is performing breast tissue regeneration while the layer 1204b is not tensioned and not yet performing the tissue regeneration of the cell growth cycle. The remaining layers 1204c-1204f are in a tensioned stage.

During the stage 1200c, the scaffold implant 1202 includes all layers in the untensioned state. Specifically, the layers 1204a-1204e are not tensioned and are performing tissue regeneration while the layer 1204f is not performing tissue regeneration.

The consecutive release of each layer 1204 of the scaffold implant 1202 may be aligned to the speed of tissue regeneration within each layer 1204 and the corresponding cell growth cycle.

Figures 13A, 13B:
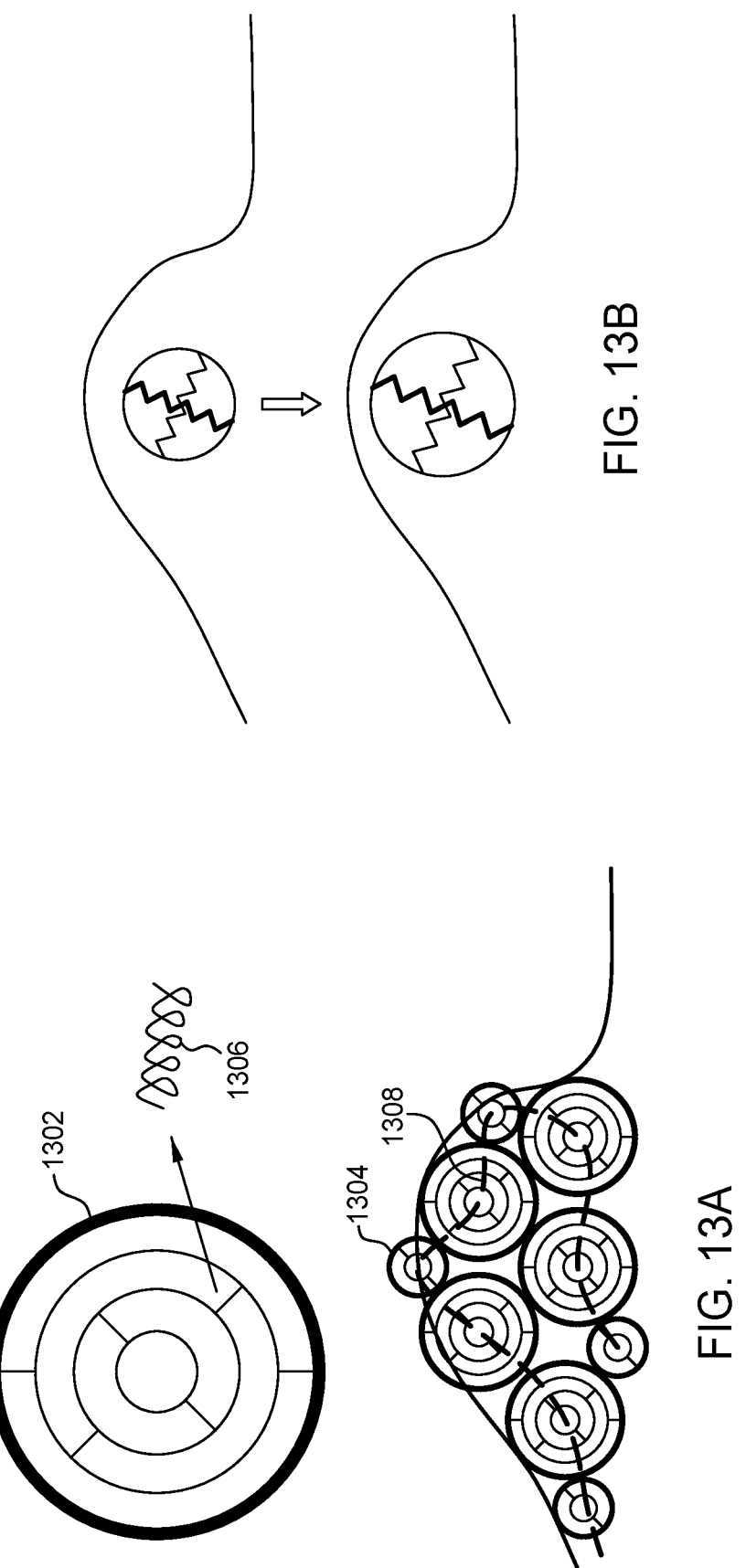
FIGS. 13A and 13B depict different embodiments of using scaffold implants to regenerate tissue at an implant location, in accordance with exemplary embodiments.

FIGS. 13A and 13B depict different embodiments of using scaffold implants 1302 to generate tissue at an implant location. As shown in FIG. 13A, the scaffold implant 1302 may comprise a domed shape based on a scan of the patient's body and the location for the implant. The scaffold implant 1302 may comprise a center that is empty space (corresponding to the empty space discussed above) such that the empty space may be filled with smaller components or layers (referred to herein as units) 1304 and/or microscopic elements which may be spherical, egg-shaped, sea urchin-shaped, or any other substantially round shape. The smaller unit 1304 may have one or more varying parameters, such as thickness, size, material, porosity, and the like. Thus, there may be many smaller units 1304 of different sizes, and so forth.

In some embodiments, the location of the scaffold implant (for example, the corresponding empty space to be filled with the scaffold implant 1302), which normally is filled with the scaffold implant 1302, may be filled with a plurality of the smaller units 1304 alone. In some embodiments, the smaller units 1304 may comprise one or multiple geometrically similar shells or other structures. These structures can be the same size or of different sizes. The smaller units 1304 may be connected by connecting elements such as springs 1306 or similar connectors, such as shown in the top portion of FIG. 13A. In certain embodiments, the smaller units 1304 are seeded with cells in accordance to the desired cellular differentiation. Such seeding may occur when the scaffold implant 1302 is implanted into the patient, such that the seeded cells and tissue are chemically activated.

In some embodiments, the connecting elements may absorb a mechanical load or maintain tension on one or more of the smaller units 1304. In certain embodiments, the connecting elements that are made of bioresorbable material(s) may loosen over time due to resorption of the connecting elements. Thus, the rate of resorption of the smaller units 1304 is controlled and the surface area of the smaller units 1304 is increased over time. As such, FIG. 13B shows a smaller unit 1304 in the top portion and a smaller unit 1304 with an increased surface area in the bottom portion. In some embodiments, the smaller unit 1304 may have a high elastic modulus to isolate its contents from external or internal mechanical influences. Furthermore, the varying thickness of the smaller units 1304 may create a gradual resorption of the scaffold implant 1302 comprising the smaller units 1304, whereby the mechanically isolated chambers of the smaller units 1304 may increase in size as the smaller units 1304 resorb. One or more of the smaller units 1304 may fill the empty space of the native tissue, depending on one or more of the cell densities, volume to be filled, placement of the scaffold implant(s), and so forth. In certain embodiments, the smaller units 1304, when multiple fill the empty space, may be connected to each other via additional connecting elements such as thread-like structures 1308, loaded in a mesh to hold them together in the central empty space, or via tubular channels, such as shown in the bottom portion of FIG. 13A. In certain embodiments, the smaller units 1304 are able to move with respect to each other, which gives the collection of smaller units 1304 in its entirety a flexibility independent of the individual smaller unit flexibilities.

FIG. 14 shows an embodiment of the scaffold implant 1402 comprising a flexible outer shell 1404 surrounding a plurality of spherical chambers 1406. In some embodiments, the scaffold implant 1402 is an embodiment of FIG. 13. The scaffold implant 1402 may correspond to the scaffold implant 300 and comprise any of the scaffold implant features described herein. In some embodiments, the scaffold implant 1402 may comprise of the outer shell 1404 that acts as a protective, flexible layer for the structure, empty space, and tissue cells deposited therein. Furthermore, the outer shell 1404 may be filled with one or more of the spherical chambers 1406 (which may also correspond to or comprise a bioresorbable, smaller units that mimic bioreactors). The spherical chambers 1406 may be interspersed with spheres containing even smaller units that have a low E modulus to reduce load and promote cell growth. One or more of the spherical chambers 1406 may be connected to each other with one or more connecting elements 1408, such as channels, wires, glue, and the like. In some instances, the resorption rate of these smaller units may be aligned with the cell growth cycle such that the outermost shell remains intact and is resorbed last after appropriate cell confluency has been achieved in the spherical chambers 1406 or on the smaller scaffold units.

FIG. 15 depicts a scaffold implant 1502 comprising a plurality cells deposited therein. For example, the scaffold implant 1502 may be dome shaped (or shaped in response to the scan of the implant location in the patient). The scaffold implant 1502 may comprise a central empty space that can be filled in. In certain embodiments, the central empty space may be filled with cells based on one or more of a density, a volume, and/or a lineage differentiation, where the cells are deposited together in one or more spherical beads 1504, such as shown in FIG. 15. The spherical beads 1504 may be used for lipofilling. In some embodiments, the spherical beads 1504 may be pre-loaded into the scaffold implant 1502 or may be loaded after the empty scaffold implant 1502 has been implanted and some level of vascularization has been achieved. Thus, the implanting of the scaffold implant 1502 and the subsequent lipofilling may be completed in one or more sessions.

FIG. 16 depicts a scaffold implant 1602 comprising one or more additional branch-like structures 1604 (similar to branches of the lung), in accordance with exemplary embodiments. In some embodiments, the additional structures 1604 resemble a tree or lung structure or anatomy, having one or more branch or bronchiole like structures. Such additional structures 1604 may guide cell deposition so that homogenous distribution of cells is achieved. In some embodiments, the additional structures 1604 comprise microscopic elements that are customized with respect to their porosity and/or density such that the microscopic elements permit attachment of certain cells and/or cells with certain parameters. For example, pigmented cells, such as green fluorescent protein (GFP) cells, may be loaded into the scaffold implant 1602 to allow ease of tracking of the tissue cells over and/or through the various additional structures 1604. In other embodiments, contrast substances or a radiopaque liquid may be used to track the tissue cells on different imaging modalities such as X-ray, CT, MRI or ultrasound.

FIG. 17 depicts a scaffold implant 1702 having one or more connecting elements 1704 between microscopic elements of the scaffold implant 1702. The scaffold implant 1702 may be an alternate embodiment of the scaffold implant 1602. For example, the scaffold implant 1702 may correspond to the scaffold implant 300 or other embodiments described herein. The connecting elements 1704 may be tubular channels or the like laid between the microscopic elements of the scaffold implant 1702 as a mesh or the like. In some embodiments, the connecting elements 1704 may be hollow, partially hollow, filled having channels, and the like. In some embodiments, the connecting elements 1704 may be loaded with an axial blood vessel while the rest of the scaffold implant 1702 is loaded with lipofilling and/or tissue cells. In certain embodiments, the connecting element 1704 allows blood connections to be easily established, thereby promoting gaseous exchange so that the surrounding cells may grow and proliferate efficiently.

Figure 18:
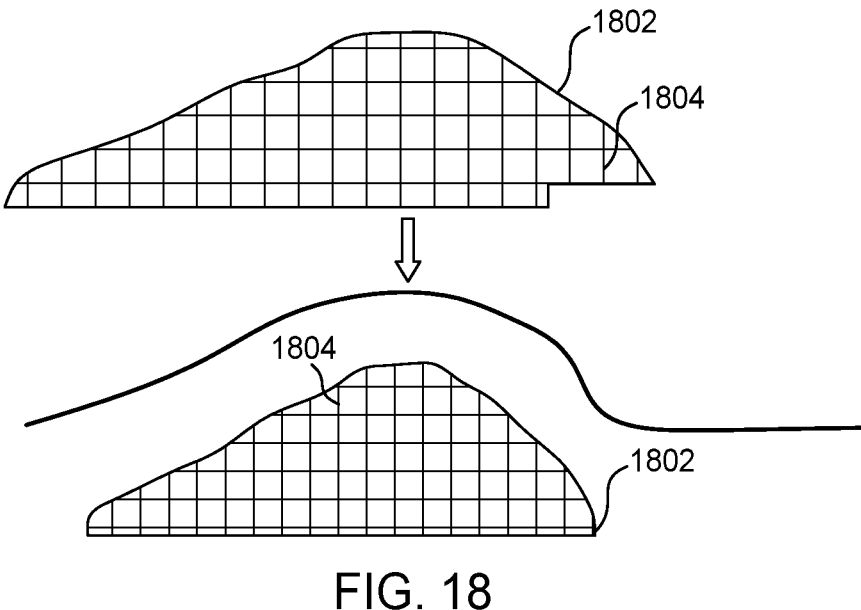
FIG. 18 depicts a scaffold implant comprising one or more macroscopic elements as implanted into a patient, in accordance with exemplary embodiments.

FIG. 18 depicts a scaffold implant comprising one or more macroscopic elements 1804 as implanted into a patient. In some embodiments, the scaffold implant may comprise the macroscopic elements 1804 that resemble a sponge (for example, that are compressed) but that may expand over time, as shown in FIG. 18. In some instances, the macroscopic element 1804 may comprise microscopic elements such as pores, cavities, or chambers of one or more varying size. The expansion force of the macroscopic element 1804 may promote cell growth. Furthermore, the macroscopic element 1804 being elastic in nature may closely resemble the native tissue being replaced or generated and, upon complete release, enable the scaffold implant to achieve the desired shape of the breast tissue. As introduced above, the scaffold implant may be inserted under pressure and released and/or resorbed over time, as shown in FIG. 18, where the released version is shown above the inserted version under pressure.

Figure 19:
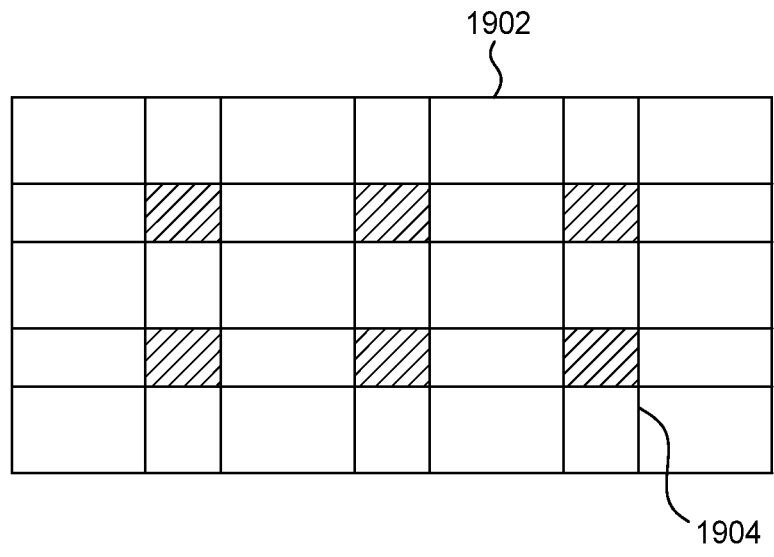
FIG. 19 depicts a scaffold implant comprising one or more macroscopic elements that resemble blocks, in accordance with exemplary embodiments.

FIG. 19 depicts a scaffold implant 1902 comprising one or more macroscopic elements 1904 that resemble blocks. In some embodiments, the scaffold implant 1902 may be an embodiment of the scaffold implant 1802. In certain embodiments, the macroscopic elements 1904 have connecting elements, such as protrusions, which allow one or more of the macroscopic elements 1904 to be connected with other macroscopic elements 1904 like interlocking bricks or pieces, as shown in FIG. 19. In some embodiments, the macroscopic elements 1904 may vary in one or more of thickness, density, porosity, material, and the like. Furthermore, the scaffold implant 1902 comprising the macroscopic elements 1904 may come in standard sizes but may be customizable by attaching the desired number of macroscopic elements 1904 to create the scaffold implant 1902. The outermost layer of the structure of the scaffold implant 1902 may comprise one or more anchoring elements such as struts, hooks, glue, and the like to act as attachment points for the scaffold implant 1902 to adhere to the surrounding native tissue. In some embodiments, the macroscopic elements 1904 may collectively or individually be pre-seeded with cells or the cells may be seeded in multiple sessions post vascularization has been established.

Scaffold Implant and Tissue Flaps

In some embodiments, the scaffold implant described herein may include a plurality of layers and one or more of the plurality of layers comprise alternating scaffold and tissue flap layers.

Figure 20A:
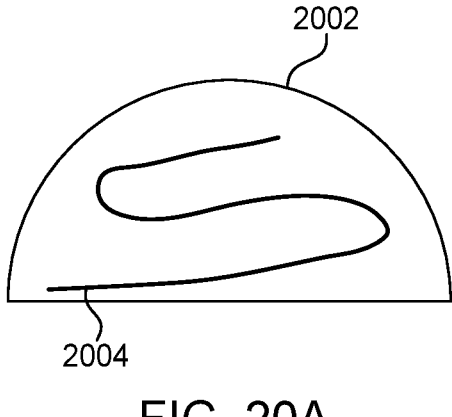
FIGS. 20A-C depict examples of the scaffold implant and the tissue flap for a breast tissue regeneration application.
Figure 20B:
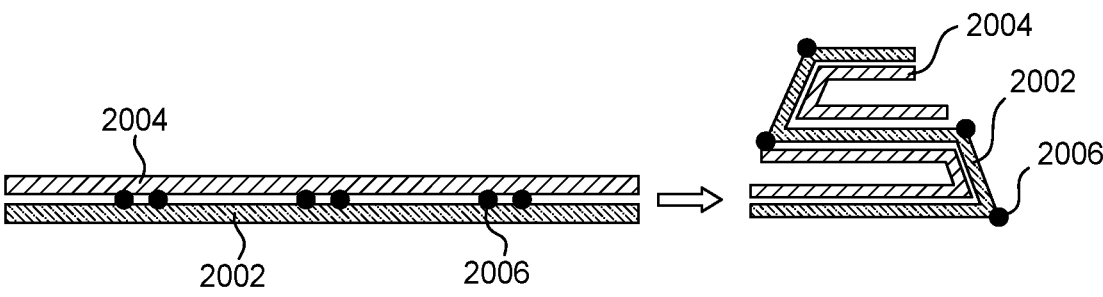
Figure 20C:
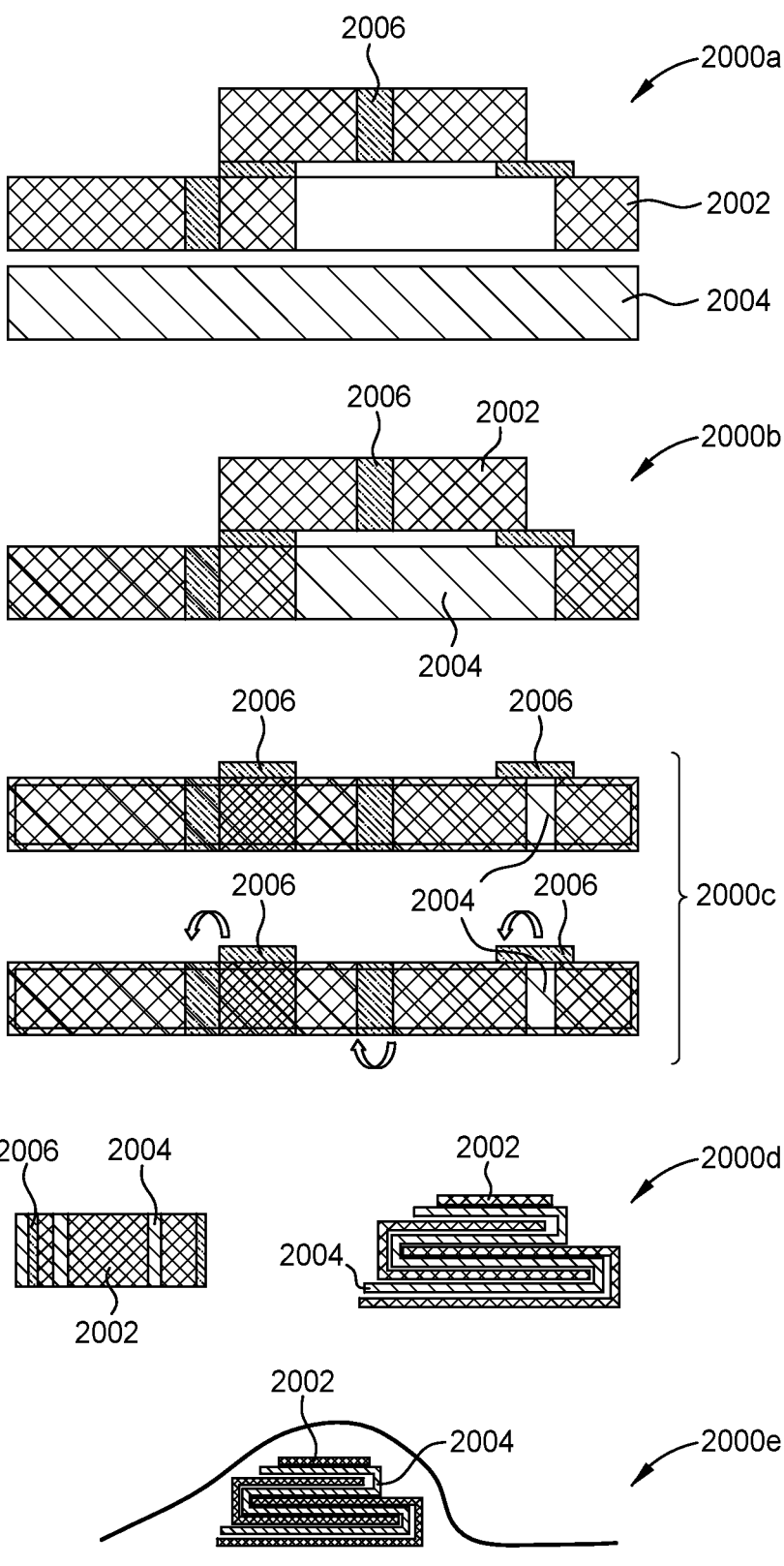

FIGS. 20A-C depict examples of the scaffold implant 2002 and the tissue flap 2004 for a breast tissue regeneration application. The scaffold implant 2002 may comprise a plurality of layers wherein the layers comprise alternating scaffold and tissue flap layers. These alternating layers enable various (or all) portions of the scaffold implant to be in close proximity to a tissue flap and its blood vessels. The tissue flap and its blood vessels may help provide nutrient transport, vascularization, and tissue regeneration within the portions of the scaffold implant 2002 (or entirety of the scaffold implant 2002) that are in close proximity to the tissue flap. In some embodiments, the scaffold implant 2002 with the intertwined layers/portions and tissue flaps may be used at the donor site to capture new tissue. Depending on the application site and available donor sites, the tissue flap 2004 may be vascularized or non-vascularized. Depending on the tissue to be regenerated, the tissue flap 2004 may comprise one or more of a fat flap, an omental flap, a fascial flap, a muscle flap, a periosteal flap, and/or a corticoperiosteal flap.

In some embodiments, the alternating layers of portions of the scaffold implant 2002 and the tissue flap 2004 are coupled using one or more connecting elements, such as surgical wires or the like. Such connecting elements may enable the scaffold implant 2002 and the tissue flap 2004 to not shift or move too much relative to each other. Furthermore, the scaffold implant 2002 may comprise components that are held together by one or more coupling features, such as external fixation plates, screws, and/or sutures.

In some embodiments, as shown in FIG. 20A, the scaffold implant 2002 may intertwine with the tissue flap 2004 in a multi-layered fashion, which may enable more portions of the scaffold implant 2002 to be in the close proximity with the tissue flap 2004. As shown, the tissue flap 2004 may be folded and inserted into the scaffold implant 2002. Alternatively, instead of folding and inserting the tissue flap 2004 in the scaffold implant 2002, the tissue flap 2004 and the scaffold implant 2002 may be folded together using a hinge 2006 (as shown in FIG. 20B) or similar component and held together with connecting elements, such as the one or more coupling features introduced above. Such use of hinges 2006 (or similar components) may enable the folded tissue flap 2004 and the scaffold implant 2002 to be held in close proximity for more portions of the scaffold implant 2002.

In some embodiments, such as FIG. 20B, the hinges 2006 or similar components and/or the coupling features comprise locking features that may be used to lock the scaffold implant 2002 with the tissue flap 2004 in its final position. The plurality of layers of portions of the scaffold implant 2002 and the tissue flap 2004 may protrude into one another. For example, in the folded embodiment shown in FIG. 20A, one or more portions of the scaffold implant 2002 surround a portion of the tissue flap 2004 for each layer or portion of the tissue flap 2004. Thus, both portions of the scaffold implant 2002 may have local protrusions into the portion of the tissue flap 2004 that provide local fixation between portions of the scaffold implant 2002 and the corresponding portion of the tissue flap 2004 and, thus, an increased surface area for any interface between the scaffold implant 2002 and the tissue flap 2004.

In some embodiments, an embodiment comprising a combination of the domed scaffold implant 2002 of FIG. 20A combined with the folding of the portions of the scaffold implant 2002 with the portions of the tissue flap 2004 shown in FIG. 20B. Other embodiments may comprise different arrangements of the portions of the scaffold implants 2002 with the portions of the tissue flap 2004. FIG. 20C shows top and side views of creating the combination of portions of the scaffold implant 2002 with the portions of the tissue flap 2004. As shown, the portions of the scaffold implant 2002 including the hinges 2006 and the tissue flap 2004. FIG. 20C provides a progression of views 2000*a*-2000*e* to create the folded and inserted embodiment of layered portions of the scaffold implant 2002 and the tissue flap 2004. The progression of views 2000*a*-2000*e* includes a first view 2000*a* of the portion of the scaffold implant 2002 with the hinges 2006 separate from the portion of the tissue flap 2004 in a flat layout separate from one another. The progression includes a second view 2000*b* of the portion of the scaffold implant 2002 with the portion of the tissue flap 2004 laid on top of the portion of the scaffold implant 2002. A third view 2000*c* of the progression includes folding steps of folding a portion of the scaffold implant 2002 using a subset of the hinges 2006 over a portion of the tissue flap 2004. A fourth view 2000*d* of the progression shows how a fully folded scaffold implant 2002 and tissue flap 2004 using the hinges 2006 can look, with a fifth view 2000*e* showing the completed folded and intertwined scaffold implant 2002 and the tissue flap 2004 implanted.

In certain embodiments, the combination of the scaffold implant 2002 with the tissue flap 2004 in the folded arrangement may result in improved tissue generation in various applications. For example, the desired macroscopic shape for the target application may vary, such as the dome shaped scaffold implant 2002 (with folded tissue flap 2004) for breast tissue reconstructions and similar applications, a cylindrical shaped scaffold implant 2002 (with the integrated tissue flap 2004) for bone applications, a cuboid shaped scaffold implant 2002 (with the integrated tissue flap 2004) for ligament/tendon applications, a semicircle shaped scaffold implant 2002 (with the integrated tissue flap 2004) for joint applications, and/or the like. The combination of scaffold implant 2002 with the tissue flap 2004 may provide improved results of successful implants in such various applications. In certain embodiments, the scaffold implant 2002 with the tissue flap 2004 in their folded arrangement enables easy surgical insertion into the anatomy. In certain embodiments the scaffold implant 2002 integrated with the tissue flap 2004 in its entirety may be flexible, eliminating the need for any additional connecting elements, as the scaffold implant 2002 may adapt its shape to the intertwining tissue flap and its surroundings.

In some embodiments, the multilayered scaffold implant 2002 and the tissue flap 2004 may be constructed intra-operatively and pre-tensioned depending on where and how it will be implanted into the patient. Once implanted into the patient, the scaffold implant 2002 and the tissue flap 2004 may be expanded over time into the desired shape (for example, through manual mechanical or chemical manipulation or resorption of coupling pieces as described herein) while the tissue flap 2004 continues to regenerate and vascularize. As introduced above, the surface of the scaffold implant 2002 may be treated to promote cell proliferation and differentiation such that the tissue flap 2004 continues to tissue regenerate while avoiding undesired effects such as calcification. In some embodiments, the multilayered scaffold implant 2002 and the tissue flap 2004 may be used for in-vitro tissue generation where the entire mature, desired tissue is then transplanted at the implant site.

For bone applications, the tissue flap 2004 may be a vascularized corticoperiosteal flap that is able to provide an uninterrupted blood supply to the portion of the bone being repaired or replaced. Thus, the multilayered scaffold implant 2002 and the tissue flap 2004 introduced above may be designed to resemble the microenvironment of the bone, such as giving the scaffold implant 2002 the cylindrical shape (or similar shape, such as a rounded triangular prism, a cylinder-like shape that more closely resembles the shape of normal bone anatomy), with alternating scaffold implant 2002 and tissue flap 2004 layers. In some instances, the tissue flap 2004 may be inserted in the core or center empty space of a cylindrical scaffold implant 2002 where a medullary cavity of the bone would be situated in normal bone anatomy. Such an arrangement may favor an outward centrifugal blood flow throughout the surrounding scaffold implant 2002 in a direction from the endosteum to the periosteum. Furthermore, the tissue flap 2004 may be enclosed within the cylindrical scaffold implant 2002 (for example, "sandwiched" between portions of the cylindrical scaffold implant 2002) to form a multi-layer construct. One embodiment of such a contrast may comprise more than one tissue flap 2004, such as an embodiment with one corticoperiosteal flap in the medullary cavity, one periosteal flap in the sandwiched position within the cylindrical scaffold implant 2002, and one extrinsic muscle flap. In some embodiments, the tissue flap 2004 selected for a particular application may be selected based on the potential for that tissue flap 2004 to stimulate tissue regeneration in the target region. For example, the intrinsic periosteal flap may be selected for its significant neo-osteogenic potential through its host-derived osteogenic growth factors, high density MSCs, and appropriate extracellular environment. The corticoperiosteal flap may be selected based on its protection of the cambium layer from surgically created tissue trauma. The muscle flap may be selected based on being an extrinsic random-pattern source of vascularization and osteogenesis.

Figure 20D:
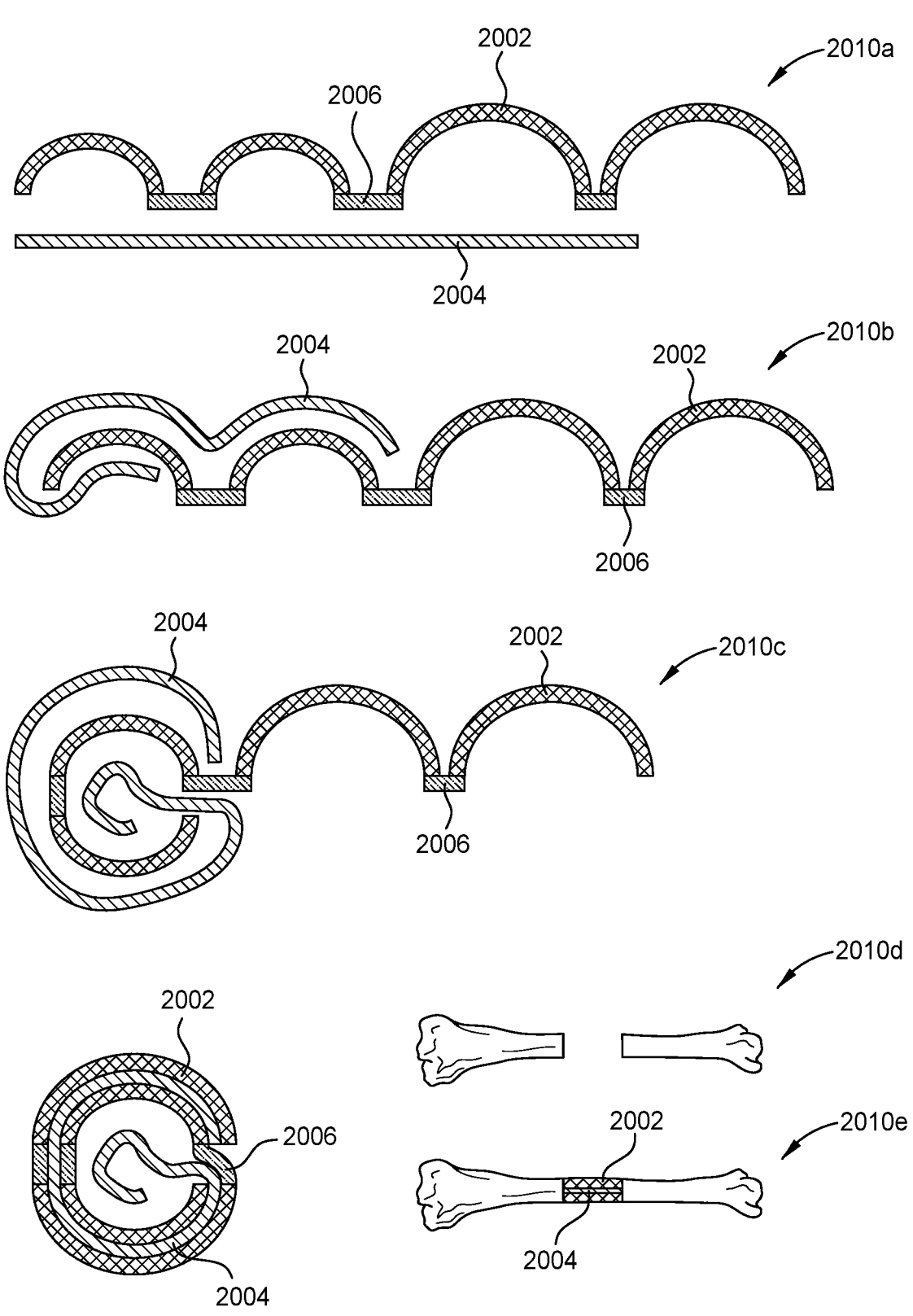
FIG. 20D shows an embodiment where more than one layer of the tissue flap is enclosed within the cylindrically shaped scaffold implant (such as in a sandwiched arrangement) with multiple layers of the tissue flap enclosed by portions of the scaffold implant, in accordance with exemplary embodiments.

FIG. 20D shows an embodiment where more than one layer of the tissue flap 2004 is enclosed within the cylindrically shaped scaffold implant 2002 (such as in a sandwiched arrangement) with multiple layers of the tissue flap 2004 enclosed by portions of the scaffold implant 2002. In some embodiments, a construct comprising the scaffold implant 2002 loaded with the tissue flap 2004 as shown in FIG. 20D may be used in combination with other osteosynthesis devices, such as dynamic compression plates, intramedullary nails, screws, external fixation devices, and the like to increase resistance of the construct to mechanical loads and/or forces. Alternatively, the enclosed tissue flap 2004 may be substituted for bone graft in the scaffold implant 2002.

The progression of views 2010a-2010e in FIG. 20D includes a first view 2010a of the portion of the scaffold implant 2002 with the hinges 2006 separate from the portion of the tissue flap 2004 in a flat layout. The progression includes a second view 2010b of the portion of the tissue flap 2004 being wrapped around an end of the portion of the scaffold implant 2002. A third view 2010c of the progression includes a partial folding or wrapping of the scaffold implant 2002 around the tissue flap 2004 using the hinges 2006. A fourth view 2010d of the progression provides a completed "rolled" construct of the scaffold implant 2002 and the tissue flap 2004, where the construct could be placed around a portion of the bone to be repair or reconstructed, as shown in the fifth view. In some embodiments, the construct shown in the fifth view 2010e of FIG. 20D may include elements to maintain the construct of the intertwined scaffold implant 2002 and the tissue flap 2004 in position and held together, such as surgical wire, pins, and the like.

Similar constructs of scaffold implants 2002 and the tissue flap 2004 may be applied to cartilage regeneration applications, such as for a patient's ear, nose, menisci, joints, and/or the like, using the tissue flap 2004 that is a vascularized periosteal flap. As cartilage is an avascular tissue (except for some fibrocartilage such as in the menisci of the knee), it has limited potential for repair. MSCs in periosteum are able to differentiate into chondrocytes with the potential to form cartilage in an environment subjected to the correct loading (in case of hyaline cartilage) or surrounding tissue. An example of a multi-layered construct of the scaffold implant 2002 and the tissue flap 2004 for use in cartilage regeneration can be seen in FIG. 20E.

Figure 20E:
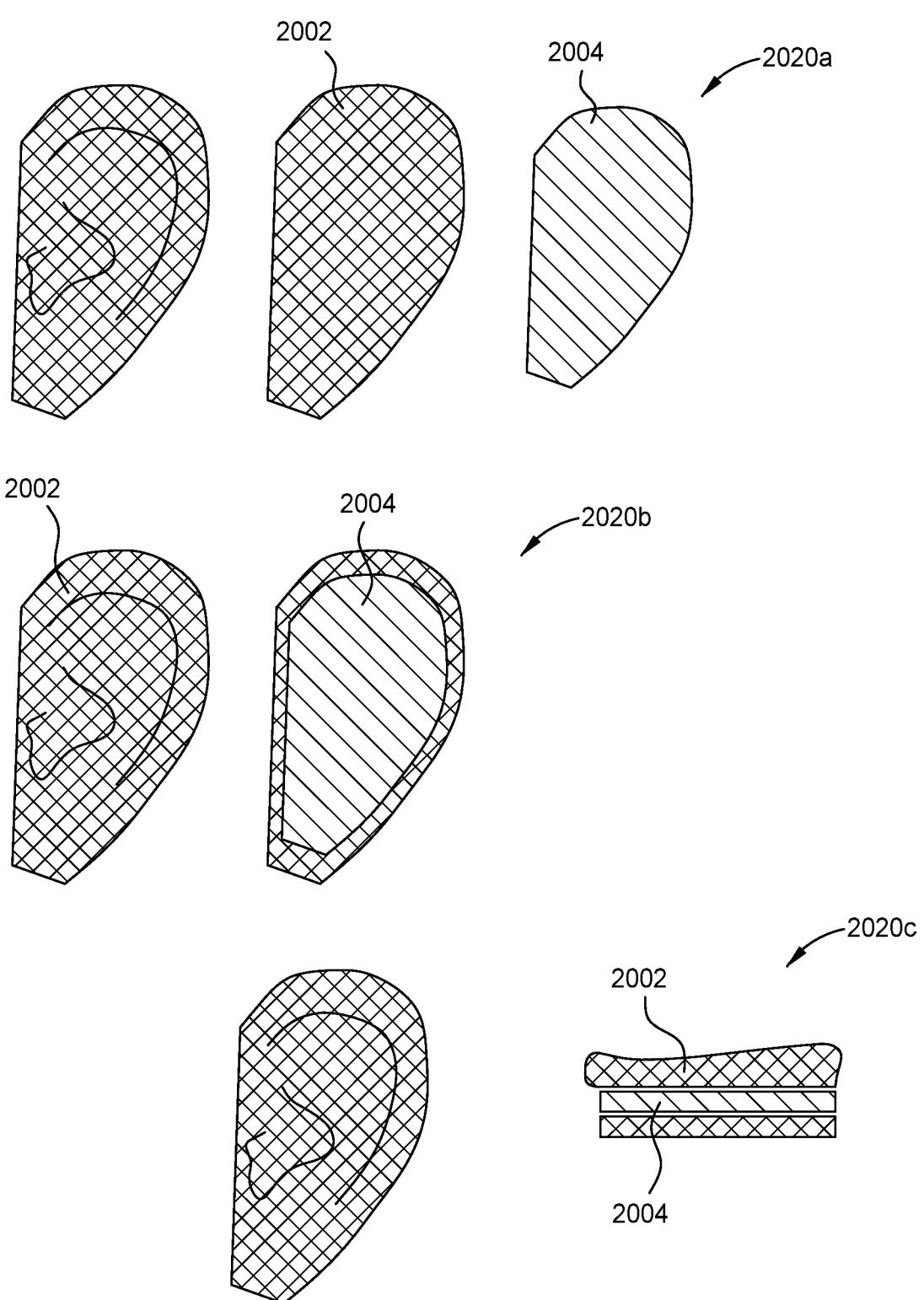
FIG. 20E shows an exemplary embodiment where one (or more) layers of the tissue flap is used with portions of the scaffold implant (such as in a sandwiched arrangement) for use in cartilage regeneration.

FIG. 20E shows an embodiment where one (or more layer) of the tissue flap 2004 to be used with portions of the scaffold implant 2002 (such as in a sandwiched arrangement) for use in the cartilage regeneration. A first view 2020a shows the two portions of the scaffold implant 2002 that form the sandwich around the tissue flap 2004 separate from the tissue flap 2004. A second view 2020b shows the tissue flap 2004 placed on top of one of the portions of the scaffold implant 2002, while the third view 2020c shows the tissue flap 2004 sandwiched between the portions of the scaffold implant 2002.

Sectioned Scaffold Implants

In some embodiments, the scaffold implant described herein can comprise a plurality of sections that are not connected until implanted into the implant site. Such construction may enhance and improve vascularization for the new tissue and attachment of the scaffold implant to the native surrounding tissue.

Figure 21A:
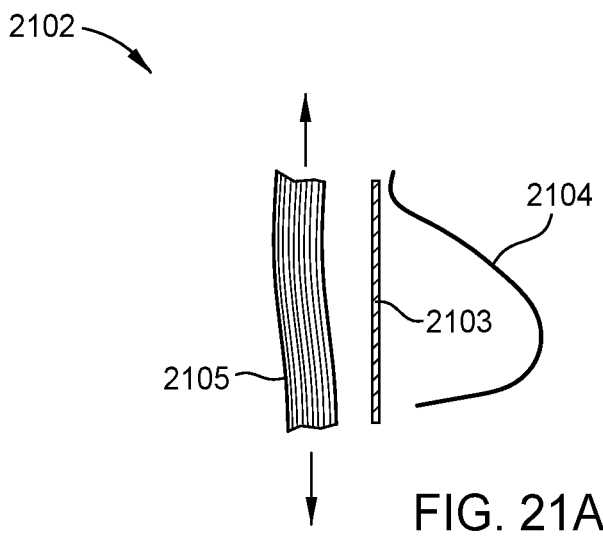
FIG. 21A depicts an example of a two piece scaffold implant having a first piece and a second piece that, together, form the scaffold implant.

FIG. 21A depicts an example of a two piece scaffold implant 2102 having a first piece 2103 and a second piece 2104 that, together, form the scaffold implant 2102. Though shown as comprising two pieces, the scaffold implant 2102 may comprise any number of separate pieces dependent, for example, on the implant site. The first piece 2103 may comprise a "bottom" piece used for attachment of the scaffold implant 2102 to the native surrounding tissue (for example, muscle) 2105, where the first piece 2103 helps maintain the native surrounding tissue 2105 in a compressed (for example, pushed down) state or condition. In some instances, the first piece 2103 layer is attached to the surrounding tissue 2105 using interfacing elements, such as surgical pins (or the like), glue (for example, biocompatible glue), and/or the like. The interfacing features may contain fibronectin, which can enhance vascularization of the new tissue. In some embodiments, the first piece 2103 comprises a microscopic element that mimics a microenvironment suited for capillary growth, such as perforated channels. The second piece 2104 may be shaped according to the volume to be filled by the new tissue. In the case of breast tissue, the second piece 2104 may comprise a dome shape. Other applications may use other shapes for the second piece 2104 of the scaffold implant 2102. In some embodiments, as introduced above, the shape of the second piece 2104 may influence cell growth and proliferation of the new tissue.

Such multi-piece scaffold implants 2102 may be utilized in surgeries such that the first piece 2103 is inserted first into the implant site to establish vascularization and the second piece 2104 is later implanted (for example, in a subsequent surgery) to fill the missing volume. In some embodiments, the second piece 2104 may be pre-seeded with cells or treated with biological/chemical agents to encourage tissue growth and proliferation. In some embodiments, the second piece 2104 is implanted "empty" and the cells or tissue can be loaded or injected in subsequent surgeries and/or procedures.

In some embodiments, the separate pieces 2103 and 2104 may be mechanically connected to each other using mechanical clips, joints, screws, nails, glue, and the like.

Figure 21B:
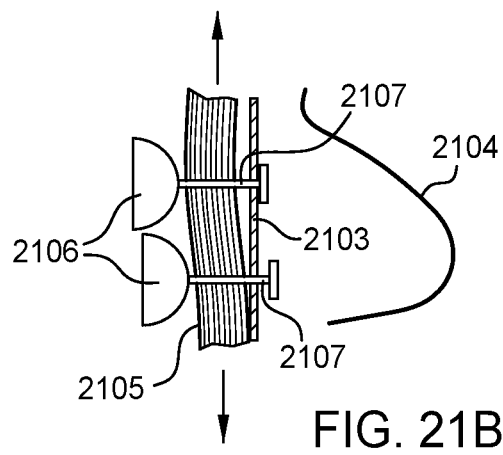
FIG. 21B depicts an example of a two piece scaffold implant for example, of FIG. 21A) as attached to host tissue or a site of tissue regeneration.

FIG. 21B depicts an example of a two piece scaffold implant for example, of FIG. 21A) as attached to host tissue or a site of tissue regeneration. The first piece 2103 may correspond to a base piece that connects to the surrounding tissue, such as the patient's ribs 2106 and surrounding tissue (for example, muscle) 2105. The ribs 2106 show two horizontal lines extending from the ribs 2106 through the native surrounding tissue 2105 and the first piece 2103, and into the second piece 2104, are clips or securing features 2107 (such as, surgical wires) that secure the ribs 2106, the muscle 2105, and the first piece 2103 together and in place.

In some embodiments, the scaffold implants described herein may be used with one or more of ASCs, fat tissue, vascularized tissue, and/or a combination thereof. In some instances, the scaffold implants may be manufactured using bioresorbable or non-bioresorbable materials, and/or a combination of both.

The embodiments described herein are exemplary in nature and are not limiting to the disclosure. Certain embodiments may be used for treatment of other diseases or defects, such as cancers of the lung, liver or for cosmetic surgeries or in combination with other existing treatments such as joint prosthesis. Certain embodiments may be used for guided tissue regeneration of other types of cells and/or tissue by customizing the scaffold implant structure to mimic the microenvironment of the native surrounding tissues.

Common Properties of Scaffold Implants

By employing a flexible scaffold design principle and diverse operation process, an additive manufacturing technique can refine and simplify the fabrication process of breast tissue.

Figure 22:
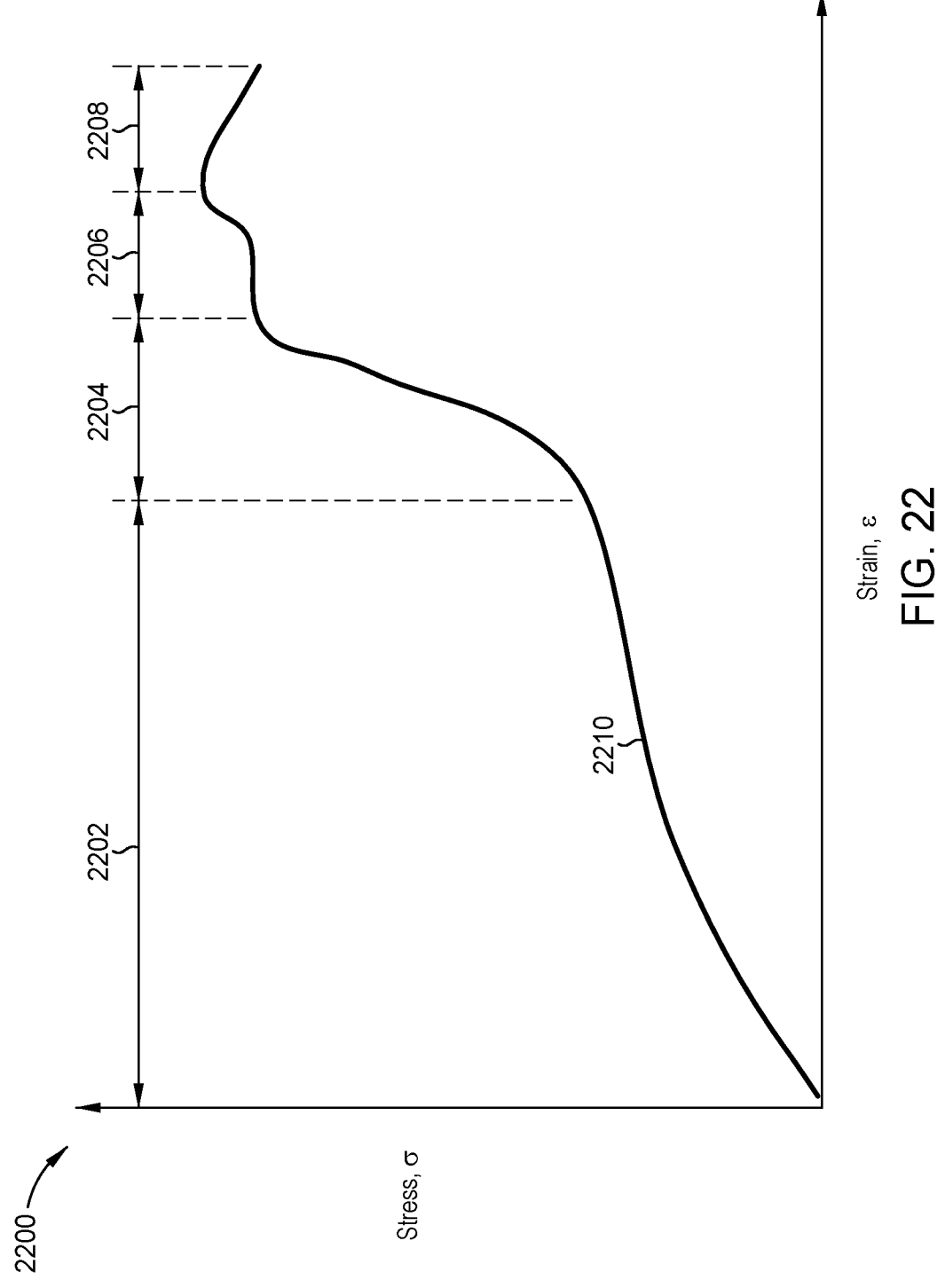
FIG. 22 provides a graph of stress (along the y-axis) as a function of strain (along the x-axis) for an exemplary scaffold implant as described herein.

FIG. 22 provides a graph 2200 of stress (along the y-axis) as a function of strain (along the x-axis) for an exemplary scaffold implant as described herein. The graph 2200 includes a stress-strain curve 2210, which displays the relationship between stress and strain for the scaffold implant. The stress-strain curve 2210 is obtained by gradually applying a load to a geometry (for example, the scaffold implant) and measuring deformation of the geometry. Based on the measured deformation of the geometry, the stress and strain can be determined and plotted to create the stress-strain curve 2210.

The graph 2200 includes four stages 2202-2208, during each of which the stress-strain curve 2210 exhibits changing behaviors or relationships between the stress and strain on the scaffold implant. For example, the first stage 2202 of the graph 2200 may represent a linear elastic stage of the architecture of the scaffold implant. During this stage, the stress-strain curve 2210 shows that the stress is substantially or generally proportional to the strain for the scaffold implant.

The second stage 2204 of the graph 2200 may represent a second linear elastic region, during which the stress is again substantially or generally proportional to the strain for the scaffold implant. However, as compared to the first stage 2202, the proportional relationship between the stress and the strain is of a different magnitude (in other words, the slope of the stress-strain curve 2210 is larger in the second stage 2204 than in the first stage 2202. In the second stage 2204, the material and the scaffold implant may experience only elastic deformation. When the second stage 2204 ends, the third stage 2206 begins.

The third stage 2206 represents a strain-hardening region, in which the stress on the scaffold implant goes beyond a yielding point, reaching a maximum stress level at an ultimate strength point. The ultimate strength point may be the maximum stress that the scaffold implant can sustain. The ultimate strength point may be called the ultimate tensile strength (UTS).

The fourth stage 2208 may also be called the necking region. When the strain exceeds the ultimate strength point (for example, beyond a tensile strength) for the scaffold implant, a neck may form where a local cross-sectional area becomes significantly smaller than the average cross-sectional area for the scaffold implant. The necking deformation may be heterogeneous and may reinforce itself as the stress concentrates more at the necking deformation.

The difference in the rigidity and shape recovery ability of the scaffold implants may be ascribed to the different geometrical shapes formed by the interconnected nodes 104 and the struts 102 in the scaffold implant.

The behavior of the architecture of the scaffold implant, as described above, is therefore beneficial for the differentiation and proliferation of particular tissue cells, such as adipose tissue, For example, for small loads (as the loads are expected in the breast area), the mechanical properties of the scaffold implant mimics the high elasticity of formed adipose tissue. At the same time, for larger loads, the mechanical properties of the scaffold implant may prevent the transduction of said stresses to the cells and jeopardize the adipogenesis process.

Figure 23:
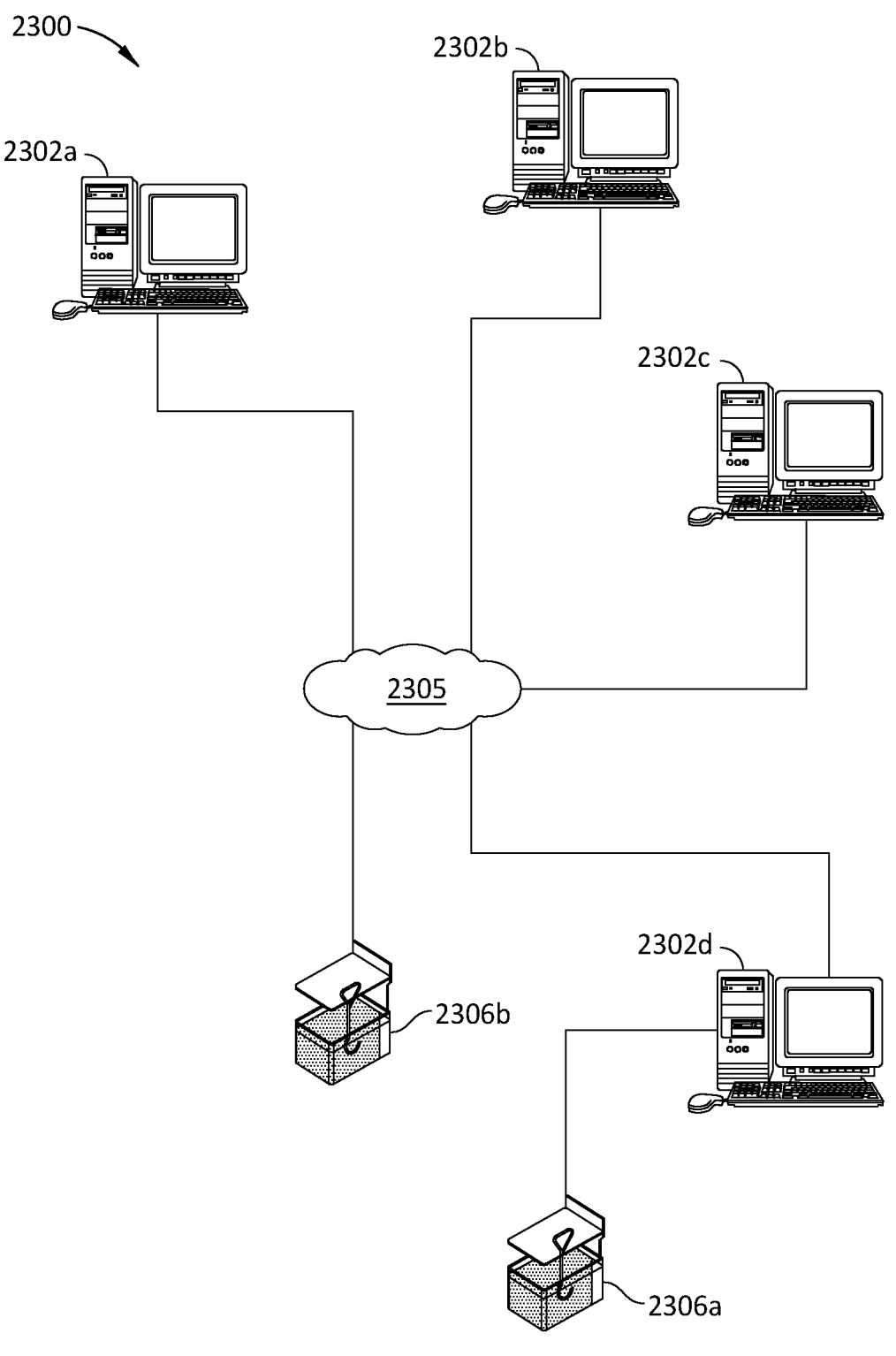
FIG. 23 is an example of a system for designing and manufacturing three-dimensional (3D) objects.

As introduced above, the scaffold implants described herein may be manufactured via 3D printing or similar additive manufacturing practices or processes. Turning to FIG. 23, an example of a computer environment suitable for implementation of 3D object (for example, the scaffold implants described herein) design, build simulation, and manufacturing is shown. The environment includes a system 2300. The system 2300 includes one or more computers 2302*a* 2302*d*, which can be, for example, any workstation, server, or other computing device capable of processing information. In some embodiments, each of the computers 2302*a*-2302*d* can be connected, by any suitable communications technology (e.g., an internet protocol), to a network 2305 (e.g., the Internet). Accordingly, the computers 2302*a*-2302*d* may transmit and receive information (e.g., software, digital representations of three dimensional (3D) objects, commands or instructions to operate an additive manufacturing device, etc.) between each other via the network 2305.

The system 2300 further includes one or more additive manufacturing devices (e.g., 3D printers) 2306*a*-2306*b*. As shown the additive manufacturing device 2306*a* is directly connected to a computer 2302*d* (and through computer 2302*d* connected to computers 2302*a* 2302*c* via the network 2305) and additive manufacturing device 2306*b* is connected to the computers 2302*a*-2302*d* via the network 2305. Accordingly, one of skill in the art will understand that an additive manufacturing device 2306 may be directly connected to a computer 2302, connected to a computer 2302 via a network 2305, and/or connected to a computer 2302 via another computer 2302 and the network 2305.

It should be noted that though the system 2300 is described with respect to a network and one or more computers, the techniques described herein also apply to a single computer 2302, which may be directly connected to an additive manufacturing device 2306.

Figure 24:
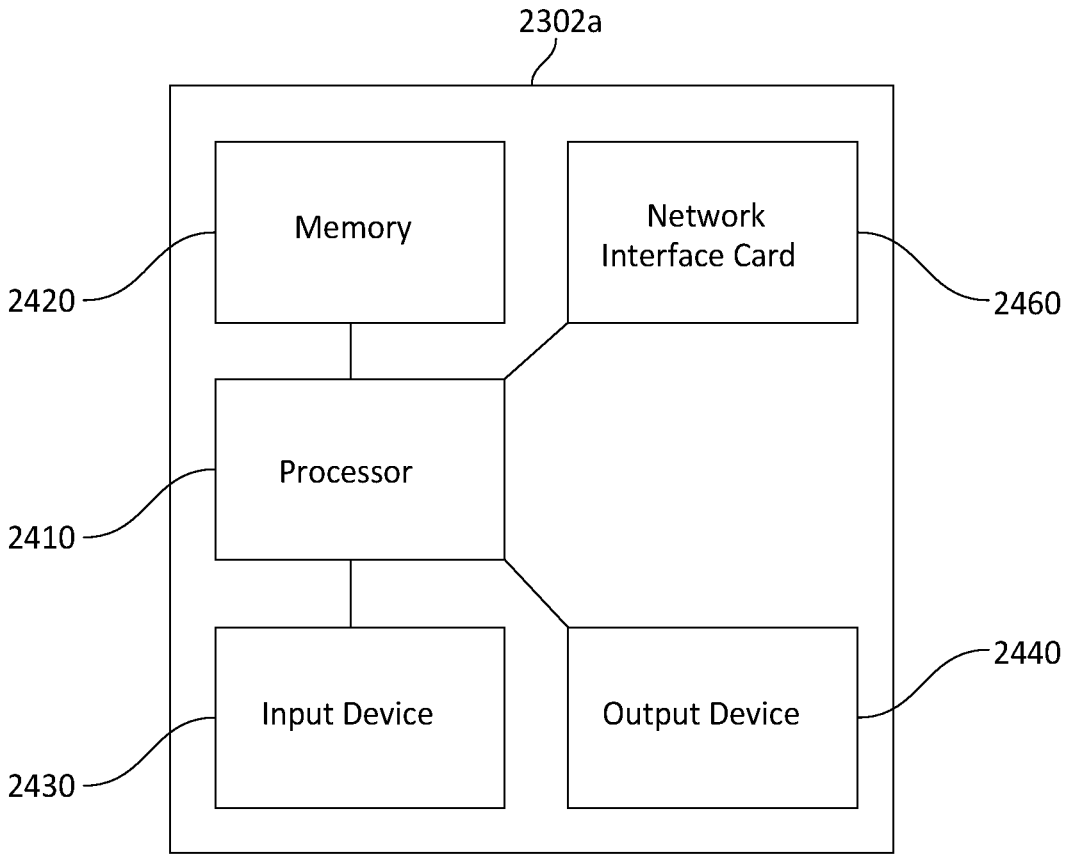
FIG. 24 illustrates a functional block diagram of one example of the computer shown in FIG. 23.

FIG. 24 illustrates a functional block diagram of one example of a computer of FIG. 23. The computer 2302*a* includes a processor 2410 in data communication with a memory 2420, an input device 2430, and an output device 2440. In some embodiments, the processor is further in data communication with an optional network interface card 2460. Although described separately, it is to be appreciated that functional blocks described with respect to the computer 2302*a* need not be separate structural elements. For example, the processor 2410 and memory 2420 may be embodied in a single chip.

The processor 2410 can be a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein. A processor may also be implemented as a combination of computing devices, e.g., a combination of a DSP and a microprocessor, a plurality of microprocessors, one or more microprocessors in conjunction with a DSP core, or any other such configuration.

The processor 2410 can be coupled, via one or more buses, to read information from or write information to memory 2420. The processor may additionally, or in the alternative, contain memory, such as processor registers. The memory 2420 can include processor cache, including a multi-level hierarchical cache in which different levels have different capacities and access speeds. The memory 2420 can also include random access memory (RAM), other volatile storage devices, or non-volatile storage devices. The storage can include hard drives, flash memory, etc.

The processor 2410 also may be coupled to an input device 2430 and an output device 2440 for, respectively, receiving input from and providing output to a user of the computer 2302*a*. Suitable input devices include, but are not limited to, a keyboard, buttons, keys, switches, a pointing device, a mouse, a joystick, a remote control, an infrared detector, a bar code reader, a scanner, a video camera (possibly coupled with video processing software to, e.g., detect hand gestures or facial gestures), a motion detector, or a microphone (possibly coupled to audio processing software to, e.g., detect voice commands). Suitable output devices include, but are not limited to, visual output devices, including displays and printers, audio output devices, including speakers, headphones, earphones, and alarms, additive manufacturing devices, and haptic output devices.

The processor 2410 further may be coupled to a network interface card 2460. The network interface card 2460 prepares data generated by the processor 2410 for transmission via a network, for example, the network 2305, according to one or more data transmission protocols. The network interface card 2460 also decodes data received via a network according to one or more data transmission protocols. The network interface card 2460 can include a transmitter, receiver, or both. In other embodiments, the transmitter and receiver can be two separate components. The network interface card 2460, can be embodied as a general purpose processor, a digital signal processor (DSP), an application specific integrated circuit (ASIC), a field programmable gate array (FPGA) or other programmable logic device, discrete gate or transistor logic, discrete hardware components, or any suitable combination thereof designed to perform the functions described herein.

Figure 25:
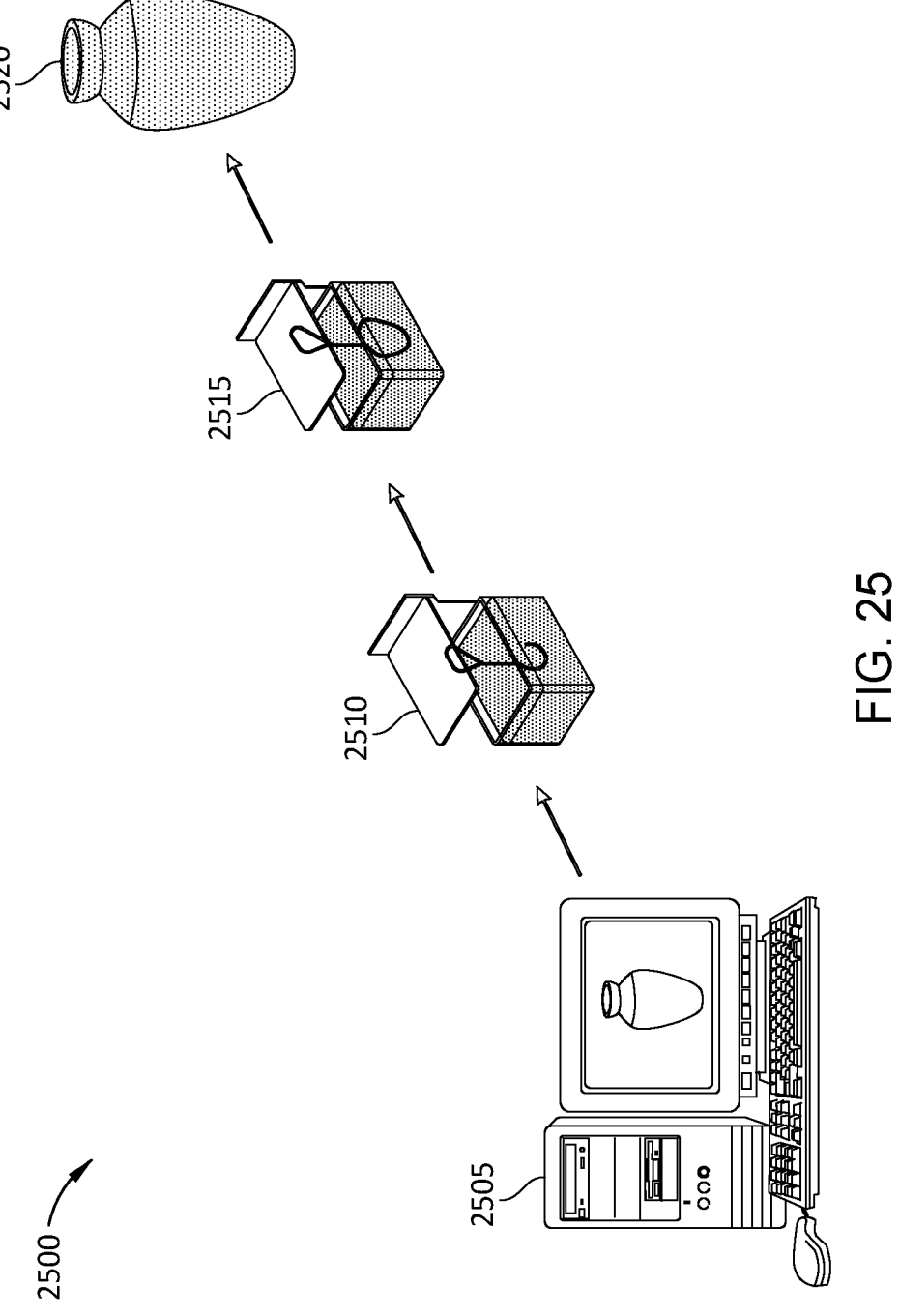
FIG. 25 illustrates a high level process for manufacturing a 3D object.

FIG. 25 illustrates a process 2500 for manufacturing a 3D object or device. As shown, at a step 2505, a digital representation of the object is designed using a computer, such as the computer 2302*a*. For example, two dimensional (2D) or 3D data may be input to the computer 2302*a* for aiding in designing the digital representation of the 3D object. Continuing at a step 2510, information corresponding to the 3D object is sent from the computer 2302*a* to an additive manufacturing device, such as additive manufacturing device 2306, and the device 2306 commences a manufacturing process for generating the 3D object in accordance with the received information. At a step 2515, the additive manufacturing device 2306 continues manufacturing the 3D object using suitable materials, such as a polymer or metal powder. Further, at a step 2520, the 3D object is generated. In some embodiments, the 3D object generated at the step 2520 is the scaffold implant described above, for example, the scaffold implant 300.

Example Clauses

Implementation examples are described in the following numbered clauses:

Clause 1: A flexible scaffold implant comprising: a plurality of layered structures, comprising: a first layered structure having a three-dimensional (3D) shape and formed from a bioresorbable material; and a second layered structure conforming to the corresponding 3D shape of the first layered structure and formed from the bioresorbable material, wherein: the first layered structure is arranged in proximity to the second layered structure, the first layered structure is configured to dissolve for resorption at a different rate than the second layered structure based on design elements of the first layered structure and the second layered structure, and the plurality of layered structures are flexible.

Clause 2: The scaffold implant of Clause 1, wherein the first layered structure and the second layered structure comprise at least one of a pore, a channel, a chamber, a strut member, a beam, or a mesh.

Clause 3: The scaffold implant of any one of Clauses 1 and 2, further comprising a tissue flap loaded, at least in part, between the first layered structure and the second layered structure.

Clause 4: The scaffold implant of Clause 3, further comprising at least one hinge configured to: couple the first layered structure to the second layered structure, and fold the first layered structure, at least in part, on top of the second layered structure such that the tissue flap is disposed between the first layered structure and the second layered structure.

Clause 5: The scaffold implant of any one of Clauses 1-4, further comprising a base element formed from the bioresorbable material, wherein the base element is configured to be coupled to at least the first layered structure and to surrounding native tissue in the patient's body.

Clause 6: The scaffold implant of any one of Clauses 1-5, further comprising a connecting structure configured to connect the first layered structure to the second layered structure, wherein the connecting structure is configured to place a force on the second layered structure relative to the first layered structure, and wherein the connecting structure is configured to dissolve to be resorbed when the force is no longer required.

Clause 7: The scaffold implant of any one of Clauses 1-6, further comprising an outer shell configured to: protect the first layered structure and the second layered structure; and dissolve for resorption after a cell confluency threshold is obtained for tissue cell growth within the scaffold implant.

Clause 8: The scaffold implant of Clause 7, further comprising one or more of a channel, a wire, or a glue configured to connect the first layered structure and the second layered structure.

Clause 9: The scaffold implant of any one of Clauses 1-8, further comprising a cell deposition structure configured to enable homogenous distribution of tissue cells within the scaffold implant.

Clause 10: The scaffold implant of Clause 9, wherein the cell deposition structure comprises microscopic elements configured to limit attachment of tissue cells to the cell deposition structure based on a cell type.

Clause 11: The scaffold implant of any one of Clauses 1-10, wherein at least one of the first layered structure or the second layered structure is configured to be implanted into the patient's body in a tensioned state and is released according to a cell growth cycle as a component maintaining the tensioned state dissolves for resorption in the patient's body or based on a chemical manipulation.

Clause 12: The scaffold implant of any one of Clauses 1-11, wherein at least one of the first layered structure or the second layered structure comprise a plurality of 3D structural elements arranged to define, at least in part, a shape and a volume of the scaffold implant, each of the 3D structural elements comprising: an arrangement of a plurality of strut members, and a plurality of nodes configured to connect at least two strut members of the plurality of strut members or a strut member of the plurality of strut members and a strut member from a neighboring 3D structural element of the plurality of 3D structural elements.

Clause 13: The scaffold implant of Clause 12, wherein the arrangement of the plurality of strut members comprises: a first number of strut members configured to connect a first number of nodes of the plurality of nodes disposed in a first layer to a second number of nodes of the plurality of nodes disposed in a third layer; a second number of strut members configured to connect the second number of nodes to a third number of nodes disposed in a second layer disposed between the first layer and the third layer; a third number of strut members configured to connect a fourth number of nodes disposed in the third layer to a fifth number of nodes in a fourth layer in a direction from the third layer opposite the second layer; and a fourth number of strut members configured to connect the second number of nodes to the fourth number of nodes.

Clause 14: The scaffold implant of Clause 12, wherein the plurality of strut members at least one of are hollow or comprise channels.

Clause 15: The scaffold implant of any one of Clauses 1-14, wherein at least one of the first layered structure or the second layered structure is configured to mimic at least one of an elasticity, a flexibility, a density, or a stiffness of a microenvironment of a location at which the scaffold implant is implanted in the patient's body.

Clause 16: The scaffold implant of any one of Clauses 1-15, wherein at least one of the first layered structure or the second layered structure is, at least in part, loaded with cells before the scaffold implant is implanted into a patient's body.

Clause 17: The scaffold implant of any one of Clauses 1-16, wherein: the scaffold implant comprises a scaffold stiffness that decreases as the first layered structure and the second layered structure dissolve; and an average of the scaffold stiffness and new tissue stiffness of new tissues that grows on the first layered structure and the second layered structure is within a threshold of a constant for each of different points along a growth cycle between deposition of the new tissue to complete dissolution of the scaffold implant.

Clause 18: The scaffold implant of any one of Clauses 1-17, wherein the bioresorbable material is configured to support tissue growth on the scaffold implant.

Clause 19: The scaffold implant of any one of Clauses 1-18, wherein an arrangement of the first layered structure and the second layered structure is compressed for implantation into a patient and subsequent expansion once the arrangement is implanted into the patient.

Clause 20: The scaffold implant of Clause 19, wherein: the expansion of the of the first layered structure and the second layered structure is aligned with a growth cycle of new tissue growth on the first layered structure and the second layered structure.

Clause 21: The scaffold implant of any one of Clauses 1-20, wherein at least one of the first layered structure or the second layered structure is integrated with one or more chemical factors configured to support or promote at least one of cell proliferation or differentiation.

Clause 22: The scaffold implant of any one of Clauses 1-21, wherein the bioresorbable material has a structural property of the bioresorbable material based on a structural property of a native tissue being replicated by the scaffold implant.

Clause 23: The scaffold implant of any one of Clauses 1-22, wherein the bioresorbable material comprises a radiopaque marker or a radiolucent material.

Clause 24: The scaffold implant of any one of Clauses 1-23, further comprising at least one deposit location for deposition of tissue cells, wherein the at least one deposit location is positioned within the scaffold implant such that the scaffold implant provides structural support for the tissue cells.

Clause 25: The scaffold implant of any one of Clauses 1-24, wherein the flexibility of the scaffold implant is based at least in part on properties of the bioresorbable material.

Clause 26: The scaffold implant of any one of Clauses 1-25, wherein the flexibility of the scaffold implant is based at least in part on the arrangement and constitution of the plurality of layered structures.

Clause 27: The scaffold implant of any one of Clauses 1-26, wherein a resorption rate of the scaffold implant is aligned with tissue regeneration promoted by the scaffold implant such that layered structures of the plurality of layered structures are replaced by regenerated tissue as the layered structures are resorbed.

Clause 28: The scaffold implant of any one of Clauses 1-27, wherein the plurality of layered structures promote tissue regeneration of one or more of breast tissue, bone tissue, cardiac tissue, and organ tissue.

Clause 29: The scaffold implant of any one of Clauses 1-28, wherein one or more of the layered structures of the plurality of layered structures is formed using additive manufacturing.

Clause 30: A method of manufacturing the scaffold implant of any one of Clauses 1-29 using an additive manufacturing process.

Clause 31: A method of regenerating tissue using the scaffold implant of any one of Clauses 1-29.

Clause 32: A processing system, comprising: a memory comprising computer-executable instructions; one or more processors configured to execute the computer-executable instructions and cause the processing system to perform a method in accordance with any one of Clauses 1-29.

Clause 33: A processing system, comprising means for performing a method in accordance with any one of Clauses 1-29.

Clause 34: A non-transitory computer-readable medium comprising computer-executable instructions that, when executed by one or more processors of a processing system, cause the processing system to perform a method in accordance with any one of Clauses 1-29.

Clause 35: A computer program product embodied on a computer-readable storage medium comprising code for performing a method in accordance with any one of Clauses 1-29.

Additional Considerations

The preceding description is provided to enable any person skilled in the art to practice the various embodiments described herein. The examples discussed herein are not limiting of the scope, applicability, or embodiments set forth in the claims. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. For instance, the methods described may be performed in an order different from that described, and various steps may be added, omitted, or combined. In addition, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, the word "exemplary" means "serving as an example, instance, or illustration." Any aspect described herein as "exemplary" is not necessarily to be construed as preferred or advantageous over other aspects.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. In addition, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A flexible scaffold implant comprising:
a plurality of layered structures, comprising:
  a first layered structure having a three-dimensional (3D) shape and formed from a bioresorbable material; and
  a second layered structure conforming to the corresponding 3D shape of the first layered structure and formed from the bioresorbable material,
wherein:
  the first layered structure is arranged in proximity to the second layered structure,
  the plurality of layered structures are flexible, and
  at least one of the first layered structure or the second layered structure comprises a plurality of 3D structural elements arranged to define, at least in part, a shape and a volume of the scaffold implant, each of the 3D structural elements comprising:
    an arrangement of a plurality of strut members, and
    a plurality of nodes configured to connect at least two strut members of the plurality of strut members or a strut member of the plurality of strut members and a strut member from a neighboring 3D structural element of the plurality of 3D structural elements,
  wherein the arrangement of the plurality of strut members comprises:
    a first number of strut members configured to connect a first number of nodes of the plurality of nodes disposed in a first layer to a second number of nodes of the plurality of nodes disposed in a third layer; and
    a second number of strut members configured to connect the second number of nodes to a third number of nodes disposed in a second layer disposed between the first layer and the third layer.

2. The scaffold implant of claim 1, further comprising an interfacing or anchoring element formed from the bioresorbable material, wherein the interfacing or anchoring element is configured to be coupled to at least the first layered structure and to surrounding native tissue in a patient's body.

3. The scaffold implant of claim 1, further comprising an outer shell configured to:
  protect the first layered structure and the second layered structure; and
  dissolve for resorption after a cell confluency threshold is obtained for tissue cell growth within the scaffold implant.

4. The scaffold implant of claim 1, further comprising a cell deposition structure configured to enable homogenous distribution of tissue cells within the scaffold implant.

5. The scaffold implant of claim 1, wherein the arrangement of the plurality of strut members further comprises:
  a third number of strut members configured to connect a fourth number of nodes disposed in the third layer to a fifth number of nodes in a fourth layer in a direction from the third layer opposite the second layer; and
  a fourth number of strut members configured to connect the second number of nodes to the fourth number of nodes.

6. The scaffold implant of claim 1, wherein at least one of the first layered structure or the second layered structure is configured to mimic elasticity, flexibility, or stiffness of a microenvironment of a location at which the scaffold implant is implanted in a patient's body.

7. The scaffold implant of claim 1, wherein at least one of the first layered structure or the second layered structure is, at least in part, loaded with cells before the scaffold implant is implanted into a patient's body.

8. The scaffold implant of claim 1, wherein an arrangement of the first layered structure and the second layered structure is compressed for implantation into a patient and subsequent expansion once the arrangement is implanted into the patient.

9. The scaffold implant of claim 1, wherein at least one of the first layered structure or the second layered structure is integrated with one or more biological or chemical factors or agents configured to support or promote at least one of cell proliferation or differentiation.

10. The scaffold implant of claim 1, wherein the plurality of strut members at least one of are hollow or comprise channels.

11. The scaffold implant of claim 1, wherein the bioresorbable material comprises a radiopaque marker or a radiolucent material.

12. The scaffold implant of claim 1, further comprising at least one deposit location for deposition of tissue cells, wherein the at least one deposit location is positioned within the scaffold implant such that the scaffold implant provides structural support for the tissue cells.

13. The scaffold implant of claim 1, wherein the flexibility of the scaffold implant is based at least in part on the arrangement and constitution of the plurality of layered structures.

14. The scaffold implant of claim 1, wherein a resorption rate of the scaffold implant is aligned with tissue regeneration promoted by the scaffold implant such that layered structures of the plurality of layered structures are replaced by regenerated tissue as the layered structures are resorbed.

15. The scaffold implant of claim 1, wherein the plurality of layered structures promote tissue regeneration of one or more of breast tissue, bone tissue, cardiac tissue, and organ tissue.

16. The scaffold implant of claim 1, wherein one or more of the layered structures of the plurality of layered structures is formed using additive manufacturing.

\* \* \* \* \*

44